US006645728B2

(12) United States Patent
Greene et al.

(10) Patent No.: US 6,645,728 B2
(45) Date of Patent: Nov. 11, 2003

(54) INHIBITOR OF THE INFLAMMATORY RESPONSE INDUCED BY TNFα AND IL-1

(75) Inventors: Warner C. Greene, Hillsborough, CA (US); Xin Lin, San Francisco, CA (US); Romas Gelezuinas, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/871,889

(22) Filed: Jun. 1, 2001

(65) Prior Publication Data

US 2002/0042499 A1 Apr. 11, 2002

Related U.S. Application Data

(62) Division of application No. 09/257,703, filed on Feb. 25, 1999, now Pat. No. 6,265,538.
(60) Provisional application No. 60/076,299, filed on Feb. 27, 1998.

(51) Int. Cl.$^7$ ...................... G01N 33/567; G01N 33/53; A61K 39/00; C07K 14/00

(52) U.S. Cl. .................... 435/7.21; 435/7.1; 424/185.1; 530/350; 530/324

(58) Field of Search ................................. 530/350, 324; 435/7.21, 7.1; 424/185.1

(56) References Cited

U.S. PATENT DOCUMENTS 5,844,073 A * 12/1998 Rothe et al. ................. 530/300

OTHER PUBLICATIONS

Alessi, Dario R. et al., "Identification of the Sites in MAP Kinase Kinase–1 Phosphorylated by p74$^{raf-1}$," *The EMBO Journal*, 1994, 13:1610–9. (Exhibit 1).
Baeuerle, Patrick A. and David Baltimore, "NF–κB: Ten Years After," *Cell*, Oct. 4, 1996, 87:13–20. (Exhibit 2).
Baldwin, Albert S., Jr. "The NF–κB and IκB Proteins: New Discoveries and Insights," *Annual Review of Immunolgy*, 1996, 14:649–83. (Exhibit 3).
Brockman, Jeffrey A. et al., "Coupling of a Signal Response Domain in IκBα to Multiple Pathways for NF–κB Activation," *Molecular and Cellular Biology*, May 1995, 15:2809–18. (Exhibit 4).
Cao, Zhaodan et al., "TRAF6 is a Signal Transducer for Interleukin–1," *Nature*, Oct. 3, 1996, 383:443–6. (Exhibit 5).
Connelly, Margery A. and Kenneth B. Marcu, "Chuk, A New Member of the Helix–Loop–Helix and Leucine Zipper Families of Interacting Proteins, Contains a Serine–Threonine Kinase Catalytic Domain," *Cellular & Molecular Biology Research*, 1995, 41:537–49. (Exhibit 6).

DiDonato, Joseph A. et al., "A Cytokine–Responsive IκB Kinase that Activates the Transcription Factor NF–κB," *Nature*, Aug. 7, 1997, 388:548–54. (Exhibit 7).
Franger, Gary R. et al., "MEK Kinases are Regulated by EGF and Selectively Interact with Rac/Cdc42," *The EMBO Journal*, 1997, 16:4961–72. (Exhibit 8).
Good, Lifeng and Shao–Cong Sun, "Persistent Activation of NF–κB/Rel by Human T–Cell Leukemia Virus Type 1 Tax Involves Degradation of IκBβ, " *Journal of Virology*, May 1996, 70:2730–5. (Exhibit 9).
Hirano, Masami et al., "MEK Kinase is Involved in Tumor Necrosis Factor α–Induced NF–κB Activation and Degradation of IκB–α," *The Journal of Biological Chemistry*, May 31, 1996, 271:13234–8. (Exhibit 10).
Hsu, Hailing et al., "TNF–Dependent Recruitment of the Protein Kinase RIP to the TNF Receptor–1 Signaling Complex," *Immunity*, Apr. 1996, 4:387–96. (Exhibit 11).
Hsu, Hailing et al., "TRADD–TRAF2 and TRADD–FADD Interactions Define Two Distinct TNF Receptor 1 Signal Transduction Pathways," *Cell*, Jan. 26, 1996, 84:299–308. (Exhibit 12).
Knaus, Ulla G. et al., "Regulation of Human Leukocyte p21–Activated Kinases Through G Protein–Coupled Receptors," *Science*, Jul. 14, 1995, 269:221–3. (Exhibit 13).
Lee, Frank S. et al., "Activation of the IκBα Kinase Complex by MEKK1, a Kinase of the JNK Pathway," *Cell*, Jan. 24, 1997, 88:213–22. (Exhibit 14).
Liu, Zheng–gang et al., "Dissection of TNF Receptor 1 Effector Functions: JNK Activation is not Linked to Apoptosis While NK–κB Activation Prevents Cell Death," *Cell*, Nov. 1, 1996, 87:565–76. (Exhibit 15).
Malinin, Nikolai L. et al., "MAP3K–Related Kinase Involved in NF–κB Induction by TNF, CD95 and IL–1," *Nature*, Feb. 6, 1997, 385:540–4. (Exhibit 16).

(List continued on next page.)

*Primary Examiner*—Yvonne Eyler
*Assistant Examiner*—J. L. Andres
(74) *Attorney, Agent, or Firm*—Mandel & Adriano

(57) ABSTRACT

The present invention provides the molecular basis for cytokine induction of NF-κB-dependent immune and inflammatory responses, emphasizing a role for both NIK-NIK and NIK-IKK protein—protein interactions. A relatively small region of NIK selectively impairs the NIK-IKK interaction. The present invention provides a novel and highly specific method for modulating NF-κB-dependent immune, inflammatory, and anti-apoptotic responses, based on interruption of the critical protein—protein interaction of NIK and IKK. The present invention provides methods for inhibiting NF-κB-dependent gene expression, using mutant NIK proteins. One embodiment of the present invention provides kinase-deficient NIK mutant proteins that inhibit activation of IKK. Another embodiment of the invention provides N-terminus NIK mutant proteins that bind IKK, thus inhibiting NIK/IKK interaction.

11 Claims, 13 Drawing Sheets

OTHER PUBLICATIONS

Mercurio, Frank et al, "IKK–1 and IKK–2: Cytokine–Activated IκB Kinases Essential for NF–κB Activation," *Science*, Oct. 31, 1997, 278:860–6. (Exhibit 17).

Muzio, Marta et al., "IRAK (Pelle) Family Member IRAK–2 and MyD88 as Proximal Mediators of IL–1 Signaling," *Science*, Nov. 28, 1997, 278:1612–5. (Exhibit 18).

Perona, Rosario et al., "Activation of the Nuclear Factor–κB by Rho, CDC42 and Rac–1 Proteins," *Genes and Development*, Feb. 15, 1997, 11:463–75. (Exhibit 19).

Regnier, Catherine H. et al., "Identification and Characterization of an IκB Kinase," *Cell*, Jul. 25, 1997, 90:373–83. (Exhibit 20).

Siow, Yaw L. et al., "Identification of Two Essential Phosphorylated Threonine Residues in the Catalytic Domain of Mekk1 Indirect Activation by Pak3 and Protein Kinase C," *The Journal of Biological Chemistry*, Mar. 21, 1997, 272:7586–94. (Exhibit 21).

Smith, Matthew R. and Warner C. Greene, "Molecular Biology of the Type 1 Human T–Cell Leukemia Virus (HTLV–I) and Adult T–Cell Leukemia," *The Journal of Clinical Investigation*, Mar. 1991, 87:761–6. (Exhibit 22).

Song, Ho Yeong et al., "Tumor Necrosis Factor (TNF)–Mediated Kinase Cascades: Bifurcation of Nuclear Factor–κB and c–jun N–Terminal Kinase (JNK/SAPK) Pathways at TNF Receptor–Associated Factor 2," *Proc. Natl. Acad. Sci. USA*, Sep. 1997, 94:9792–6. (Exhibit 23).

Sulciner, David J. et al, "rac1 Regulates a Cytokine–Stimulated, Redox–Dependent Pathway Necessary of NF–κB Activation," *Molecular and Cellular Biology*, Dec. 1996, 16:7115–7121. (Exhibit 24).

Sun, Shao–Cong et al., "Both Amino– and Carboxyl– Terminal Sequences Within IκBα Regulate Its Inducible Degradation," *Molecular and Cellular Biology*, Mar. 1996, 16:1056–65. (Exhibit 25).

Sun, Shao–Cong et al., "Human T–Cell Leukemia Virus Type I Tax Activation of NF–κB/Rel Involves Phosphorylation and Degradation of IκBα and RelA (p65)–Mediated Induction of the c–rel Gene," *Molecular and Cellular Biology*, Nov. 1994, 14:7377–84. (Exhibit 26).

Verma, Inder M. et al., "Rel/NF–κB Family: Intimate Tales of Association and Dissociation," *Genes and Development*, Nov. 15, 1995, 9:2723–35. (Exhibit 27).

Woronicz, John D. et al., "IκB Kinase–β: NF–κB Activation and Complex Formation with IκB Kinase–α and NIK," *Science*, Oct. 1997, 278:866–9. (Exhibit 28).

Yan, Minhong and Dennis J. Templeton, "Identification of 2 Serine Residues of MEK–1 That Are Differentially Phosphorylated During Activation of raf and MEK Kinase," *The Journal of Biological Chemistry*, Jul. 22, 1994, 269:19067–73. (Exhibit 29).

Zandi, Ebrahim et al., "TκB Kinase Complex (IKK) Contains Two Kinase Subunits, IKKα and IKKβ, Necessary for IκB Phosphorylation and NF–κB Activation," *Cell*, Oct. 17, 1997, 91:243–52. (Exhibit 30).

Zheng, Chao–Feng and Kun–Liang Guan, "Activation of MEK Family Kinases Requires Phosphorylation of Two Conserved Ser/Thr Residues," *The EMBO Journal*, 1994, 13:1123–31. (Exhibit 31).

Lin, Xin et al., "Molecular Determinants of NF–κB–Inducing Kinase Action," *Molecular and Cellular Biology*, Oct. 1998, 18:10:5899–5907. (Exhibit 32).

* cited by examiner

FIG. 2A
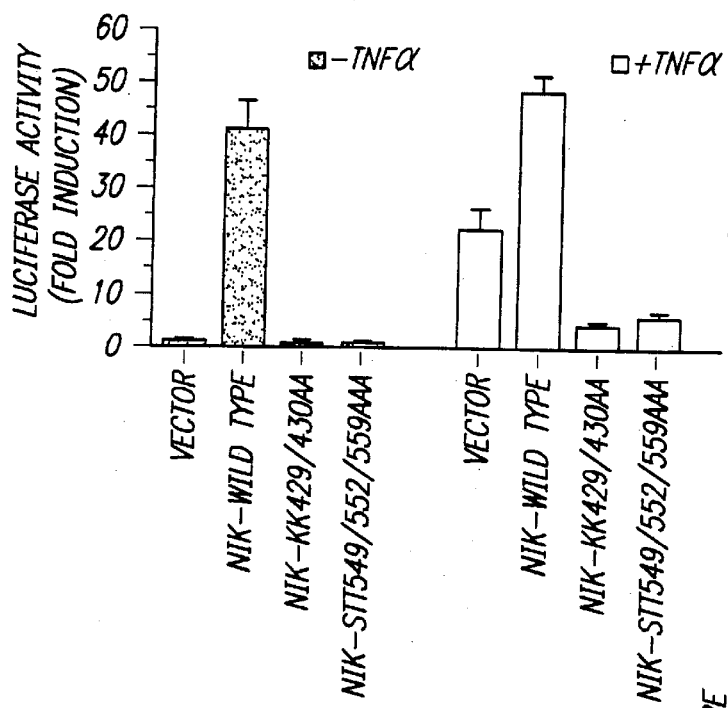
FIG. 2B
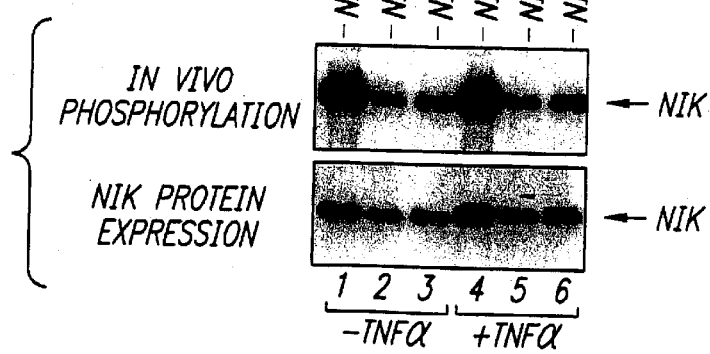
FIG. 2C

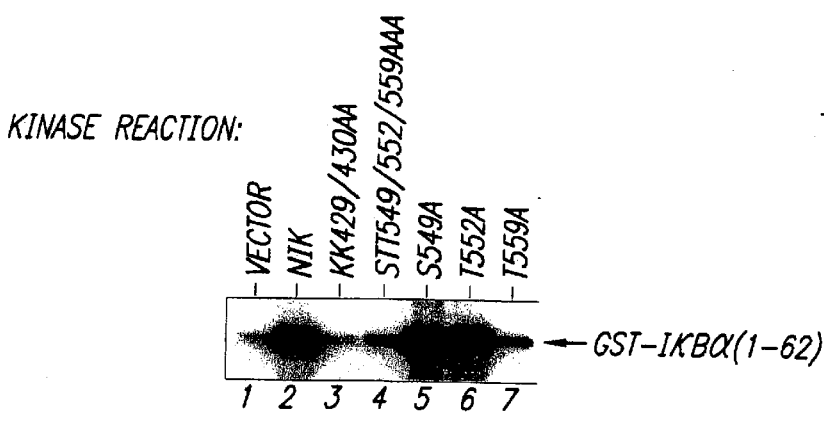
FIG. 3A
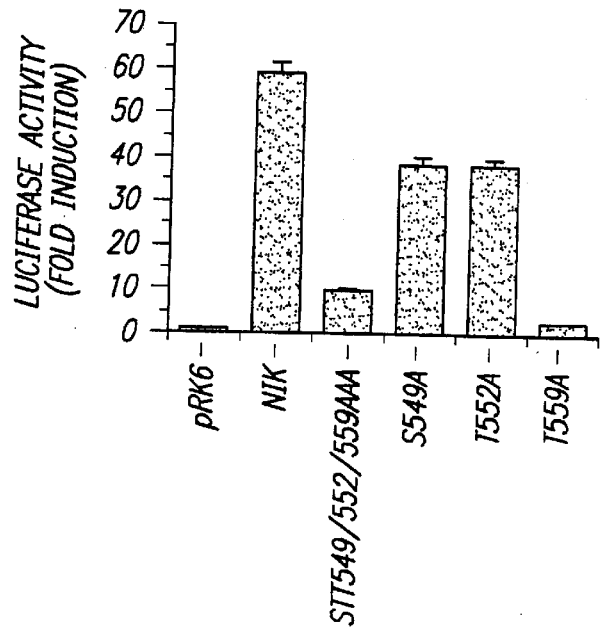
FIG. 3B
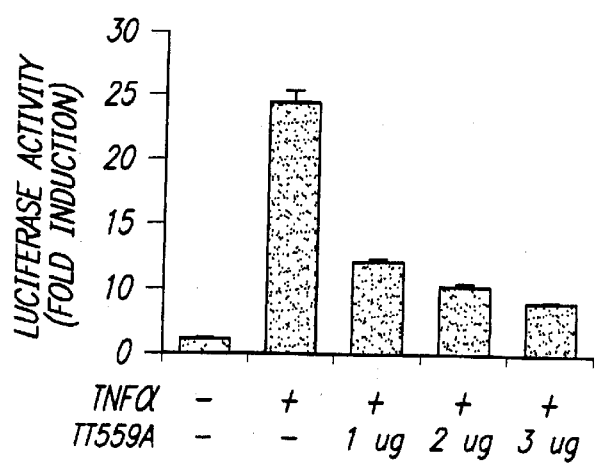
FIG. 3C

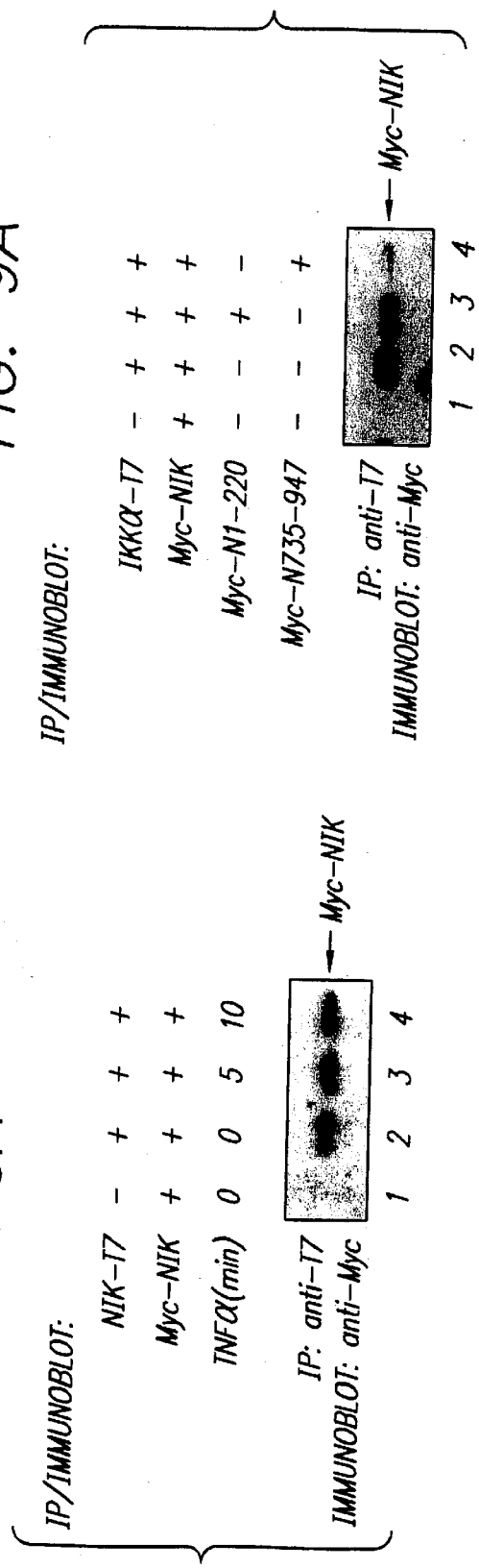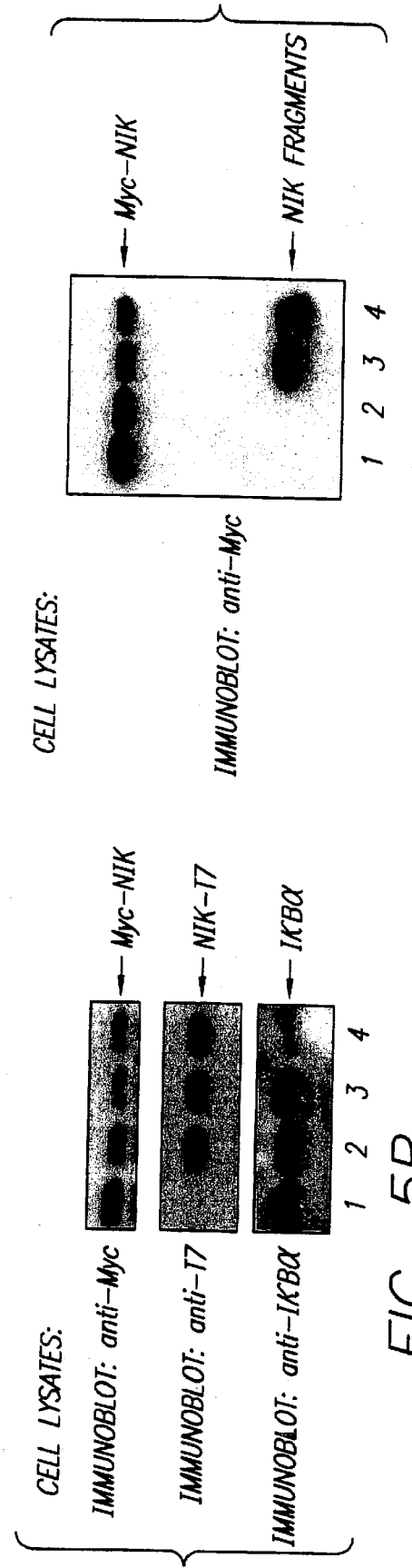

STRUCTURAL DOMAINS OF NIK:

CELL LYSATES:

IP/IMMUNOBLOT:

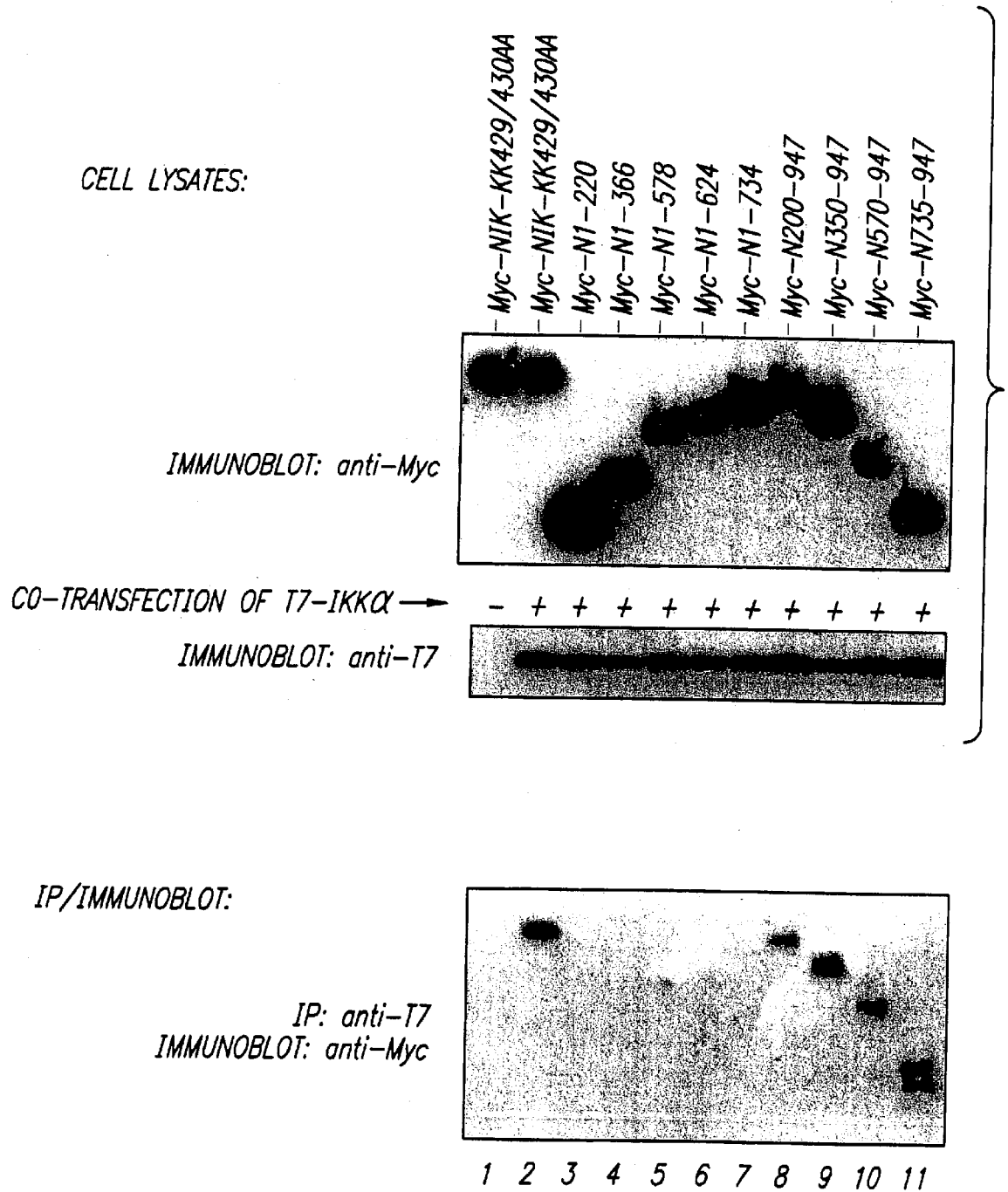

FIG. 10-1

```
1/1                                      31/11
atg gca gtg atg gaa atg gcc tgc cca ggt gcc cct ggc tca gca gtg ggg cag cag aag
 M   A   V   M   E   M   A   C   P   G   A   P   G   S   A   V   G   Q   Q   K
61/21                                    91/31
gaa ctc ccc aag cca aag gag aag acg ccg cca ctg ggg aag aaa cag agc tcc gtc tac
 E   L   P   K   P   K   E   K   T   P   P   L   G   K   K   Q   S   S   V   Y
121/41                                   151/51
aag ctt gag gcc gtg gag aag agc cct gtg ttc tgc gga aag tgg gag atc ctg aat gac
 K   L   E   A   V   E   K   S   P   V   F   C   G   K   W   E   I   L   N   D
181/61                                   211/71
gtg att acc aag ggc aca gcc aag gaa ggc tcc gag gca ggg cca gct gcc atc tct atc
 V   I   T   K   G   T   A   K   E   G   S   E   A   G   P   A   A   I   S   I
241/81                                   271/91
atc gcc cag gct gag tgt gag aat agc caa gag ttc agc ccc acc ttt tca gaa cgc att
 I   A   Q   A   E   C   E   N   S   Q   E   F   S   P   T   F   S   E   R   I
301/101                                  331/111
ttc atc gct ggg tcc aaa cag tac agc cag tcc gag agt ctt gat cag atc ccc aac aat
 F   I   A   G   S   K   Q   Y   S   Q   S   E   S   L   D   Q   I   P   N   N
361/121                                  391/131
gtg gcc cat gct aca gag ggc aaa atg gcc cgt gtg tgt tgg aag gga aag cgt cgc agc
 V   A   H   A   T   E   G   K   M   A   R   V   C   W   K   G   K   R   R   S
421/141                                  451/151
aaa gcc cgg aag aaa cgg aag aag aag agc tca aag tcc ctg gct cat gca gga gtg gcc
 K   A   R   K   K   R   K   K   K   S   S   K   S   L   A   H   A   G   V   A
481/161                                  511/171
ttg gcc aaa ccc ctc ccc agg acc cct gag cag gag agc tgc acc atc cca gtg cag gag
 L   A   K   P   L   P   R   T   P   E   Q   E   S   C   T   I   P   V   Q   E
541/181                                  571/191
gat gag tct cca ctc ggc gcc cca tat gtt aga aac acc ccg cag ttc acc aag cct ctg
 D   E   S   P   L   G   A   P   Y   V   R   N   T   P   Q   F   T   K   P   L
601/201                                  631/211
aag gaa cca ggc ctt ggg caa ctc tgt ttt aag cag ctt ggc gag ggc cta cgg ccg gct
 K   E   P   G   L   G   Q   L   C   F   K   Q   L   G   E   G   L   R   P   A
661/221                                  691/231
ctg cct cga tca gaa ctc cac aaa ctg atc agc ccc ttg caa tgt ctg aac cac gtg tgg
 L   P   R   S   E   L   H   K   L   I   S   P   L   Q   C   L   N   H   V   W
721/241                                  751/251
aaa ctg cac cac ccc cag gac gga ggc ccc ctg ccc ctg ccc acg cac ccc ttc ccc tat
 K   L   H   H   P   Q   D   G   G   P   L   P   L   P   T   H   P   F   P   Y
781/261                                  811/271
agc aga ctg cct cat ccc ttc cca ttc cac cct ctc cag ccc tgg aaa cct cac cct ctg
 S   R   L   P   H   P   F   P   F   H   P   L   Q   P   W   K   P   H   P   L
841/281                                  871/291
gag tcc ttc ctg ggc aaa ctg gcc tgt gta gac agc cag aaa ccc ttg cct gac cca cac
 E   S   F   L   G   K   L   A   C   V   D   S   Q   K   P   L   P   D   P   H
```

FIG. 10-2

```
901/301                                    931/311
ctg agc aaa ctg gcc tgt gta gac agt cca aag ccc ctg cct ggc cca cac ctg gag ccc
 L   S   K   L   A   C   V   D   S   P   K   P   L   P   G   P   H   L   E   P
961/321                                    991/331
agc tgc ctg tct cgt ggt gcc cat gag aag ttt tct gtg gag gaa tac cta gtg cat gct
 S   C   L   S   R   G   A   H   E   K   F   S   V   E   E   Y   L   V   H   A
1021/341                                   1051/351
ctg caa ggc agc gtg agc tca agc cag gcc cac agc ctg acc agc ctg gcc aag acc tgg
 L   Q   G   S   V   S   S   S   Q   A   H   S   L   T   S   L   A   K   T   W
1081/361                                   1111/371
gca gca cgg ggc tct aga tcc cgg gag ccc agc ccc aaa act gag gac aac gag ggt gtc
 A   A   R   G   S   R   S   R   E   P   S   P   K   T   E   D   N   E   G   V
1141/381                                   1171/391
ctg ctc act gag aaa ctc aag cca gtg gat tat gag tac cga gaa gaa gtc cac tgg gcc
 L   L   T   E   K   L   K   P   V   D   Y   E   Y   R   E   E   V   H   W   A
1201/401                                   1231/411
acg cac cag ctc cgc ctg ggc aga ggc tcc ttc gga gag gtg cac agg atg gag gac aag
 T   H   Q   L   R   L   G   R   G   S   F   G   E   V   H   R   M   E   D   K
1261/421                                   1291/431
cag act ggc ttc cag tgc gct gtc aaa aag gtg cgg ctg gaa gta ttt cgg gca gag gag
 Q   T   G   F   Q   C   A   V   K   K   V   R   L   E   V   F   R   A   E   E
1321/441                                   1351/451
ctg atg gca tgt gca gga ttg acc tca ccc aga att gtc cct ttg tat gga gct gtg aga
 L   M   A   C   A   G   L   T   S   P   R   I   V   P   L   Y   G   A   V   R
1381/461                                   1411/471
gaa ggg cct tgg gtc aac atc ttc atg gag ctg ctg gaa ggt ggc tcc ctg ggc cag ctg
 E   G   P   W   V   N   I   F   M   E   L   L   E   G   G   S   L   G   Q   L
1441/481                                   1471/491
gtc aag gag cag ggc tgt ctc cca gag gac cgg gcc ctg tac tac ctg ggc cag gcc ctg
 V   K   E   Q   G   C   L   P   E   D   R   A   L   Y   Y   L   G   Q   A   L
1501/501                                   1531/511
gag ggt ctg gaa tac ctc cac tca cga agg att ctg cat ggg gac gtc aaa gct gac aac
 E   G   L   E   Y   L   H   S   R   R   I   L   H   G   D   V   K   A   D   N
1561/521                                   1591/531
gtg ctc ctg tcc agc gat ggg agc cac gca gcc ctc tgt gac ttt ggc cat gct gtg tgt
 V   L   L   S   S   D   G   S   H   A   A   L   C   D   F   G   H   A   V   C
1621/541                                   1651/551
ctt caa cct gat ggc ctg gga aag tcc ttg ctc aca ggg gac tac atc cct ggc aca gag
 L   Q   P   D   G   L   G   K   S   L   L   T   G   D   Y   I   P   G   T   E
1681/561                                   1711/571
acc cac atg gct ccg gag gtg gtg ctg ggc agg agc tgc gac gcc aag gtc gac gtc tgg
 T   H   M   A   P   E   V   V   L   G   R   S   C   D   A   K   V   D   V   W
```

FIG. 10-3

```
1741/581                                    1771/591
agc agc tgc tgt atg atg ctg cac atg ctc     aac ggc tgc cac ccc tgg act cag ttc ttc
 S   S   C   C   M   M   L   H   M   L       N   G   C   H   P   W   T   Q   F   F
1801/601                                    1831/611
cga ggg ccg ctc tgc ctc aag att gcc agc     gag cct ccg cct gtg agg gag atc cca ccc
 R   G   P   L   C   L   K   I   A   S       E   P   P   P   V   R   E   I   P   P
1861/621                                    1891/631
tcc tgc gcc cct ctc aca gcc cag gcc atc     caa gag ggg ctg agg aaa gag ccc atc cac
 S   C   A   P   L   T   A   Q   A   I       Q   E   G   L   R   K   E   P   I   H
1921/641                                    1951/651
cgc gtg tct gca gcg gag ctg gga ggg aag     gtg aac cgg gca cta cag caa gtg gga ggt
 R   V   S   A   A   E   L   G   G   K       V   N   R   A   L   Q   Q   V   G   G
1981/661                                    2011/671
ctg aag agc cct tgg agg gga gaa tat aaa     gaa cca aga cat cca ccg cca aat caa gcc
 L   K   S   P   W   R   G   E   Y   K       E   P   R   H   P   P   P   N   Q   A
2041/681                                    2071/691
aat tac cac cag acc ctc cat gcc cag ccg     aga gag ctt tcg cca agg gcc cca ggg ccc
 N   Y   H   Q   T   L   H   A   Q   P       R   E   L   S   P   R   A   P   G   P
2101/701                                    2131/711
cgg cca gct gag gag aca aca ggc aga gcc     cct aag ctc cag cct cct ctc cca cca gag
 R   P   A   E   E   T   T   G   R   A       P   K   L   Q   P   P   L   P   P   E
2161/721                                    2191/731
ccc cca gag cca aac aag tct cct ccc ttg     act ttg agc aag gag gag tct ggg atg tgg
 P   P   E   P   N   K   S   P   P   L       T   L   S   K   E   E   S   G   M   W
2221/741                                    2251/751
gaa ccc tta cct ctg tcc tcc ctg gag cca     gcc cct gcc aga aac ccc agc tca cca gag
 E   P   L   P   L   S   S   L   E   P       A   P   A   R   N   P   S   S   P   E
2281/761                                    2311/771
cgg aaa gca acc gtc ccg gag cag gaa ctg     cag cag ctg gaa ata gaa tta ttc ctc aac
 R   K   A   T   V   P   E   Q   E   L       Q   Q   L   E   I   E   L   F   L   N
2341/781                                    2371/791
agc ctg tcc cag cca ttt tct ctg gag gag     cag gag caa att ctc tcg tgc ctc agc atc
 S   L   S   Q   P   F   S   L   E   E       Q   E   Q   I   L   S   C   L   S   I
2401/801                                    2431/811
gac agc ctc tcc ctg tcg gat gac agt gag     aag aac cca tca aag gcc tct caa agc tcg
 D   S   L   S   L   S   D   D   S   E       K   N   P   S   K   A   S   Q   S   S
2461/821                                    2491/831
cgg gac acc ctg agc tca ggc gta cac tcc     tgg agc agc cag gcc gag gct cga agc tcc
 R   D   T   L   S   S   G   V   H   S       W   S   S   Q   A   E   A   R   S   S
2521/841                                    2551/851
agc tgg aac atg gtg ctg gcc cgg ggg cgg     ccc acc gac acc cca agc tat ttc aat ggt
 S   W   N   M   V   L   A   R   G   R       P   T   D   T   P   S   Y   F   N   G
2581/861                                    2611/871
gtg aaa gtc caa ata cag tct ctt aat ggt     gaa cac ctg cac atc cgg gag ttc cac cgg
 V   K   V   Q   I   Q   S   L   N   G       E   H   L   H   I   R   E   F   H   R
```

FIG.-10-4

```
2641/881                                    2671/891
gtc aaa gtg gga gac atc gcc act ggc atc agc agc cag atc cca gct gca gcc ttc agc
 V   K   V   G   D   I   A   T   G   I   S   S   Q   I   P   A   A   A   F   S
2701/901                                    2731/911
ttg gtc acc aaa gac ggg cag cct gtt cgc tac gac atg gag gtg cca gac tcg ggc atc
 L   V   T   K   D   G   Q   P   V   R   Y   D   M   E   V   P   D   S   G   I
2761/921                                    2791/931
gac ctg cag tgc aca ctg gcc cct gat ggc agc ttc gcc tgg agc tgg agg gtc aag cat
 D   L   Q   C   T   L   A   P   D   G   S   F   A   W   S   W   R   V   K   H
2821/941
ggc cag ctg gag aac agg ccc taa
 G   Q   L   E   N   R   P   *
```

INHIBITOR OF THE INFLAMMATORY RESPONSE INDUCED BY TNFα AND IL-1

This application is a divisional application of U.S. Ser. No. 09/257,703, filed Feb. 25, 1999, now a U.S. Pat. No. 6,265,538, which claims benefit of U.S. Serial No. 60/076,299, filed Feb. 27, 1998.

Throughout this application various publications are referenced. The disclosures of these publications in their entireties are hereby incorporated by reference into this application in order to more fully describe the state of the art to which this invention pertains.

FIELD OF INVENTION

The present invention relates generally to the field of NF-κB-dependent activation to regulate immune, inflammatory, and anti-apoptotic responses. In particular, the present invention describes an inhibitor of serine/threonine kinase signaling that regulates NF-κB-dependent activation, thereby regulating immune, inflammatory, and anti-apoptotic responses. The present invention describes several mutant proteins of the NF-κB-inducing kinase (NIK) that prevent activation of a downstream kinase, IκB-specific kinase (IKK). One embodiment of the present invention describes kinase-deficient mutant NIK proteins that inhibits phosphorylation and activation of IKK. Another embodiment of the present invention describes an C-terminal NIK peptide protein that effectively interacts with IKK, and blocks IKK activation by inhibiting NIK/IKK association. Yet another embodiment of the present invention describes a method for inhibiting NF-κB-dependent immune and inflammatory responses using the NIK mutant proteins.

BACKGROUND OF THE INVENTION

TNFα (tumor necrosis factor alpha) binding at the plasma membrane induces intracellular signaling events that translate into the induction of NF-κB in the nucleus. The eukaryotic NF-κB/Rel (nuclear factor-κB/Rel) family of transcription factors plays an essential role in the regulation of inflammatory, immune, and apoptotic responses (Bacuerle and Baltimore 1996; Baldwin 1996; Verma et al 1995). One of the distinguishing characteristics of the NF-κB/Rel transcription factor is its posttranslational regulation through interactions with cytoplasmic inhibitory proteins termed IκB (inhibitor-κB). NF-κB corresponds to an inducible eukaryotic transcription factor complex that is negatively regulated in resting cells, by its physical assembly with a family of cytoplasmic ankyrin-rich IκB inhibitors (Bacuerle and Baltimore 1996; Baldwin 1996; Verma et al 1995). Stimulation of cells with various pro-inflammatory cytokines, including TNFα, induces nuclear NF-κB expression. The TNFα-signaling pathway is complex and involves recruitment of at least three adapter proteins, TRADD (TNF-R1 associated death domain protein) and TRAF-2 (TNF-receptor-associated factor)-2, and the serine/threonine kinase RIP (receptor interacting protein) to the cytoplasmic tail of the type 1 TNF receptor (Hsu et al Immunity 1996; Hsu et al Cell 1996) (FIG. 1). In turn, the recruitment of these factors promotes activation of the downstream NIK (Malinin et al 1997) and IKKα and IKKβ (IκB-specific kinases) (DiDonato et al 1997; Mercurio et al 1997; Regnier et al 1997; Woronicz et al 1997; Zandi et al 1997). The activated IKKα and IKKβ directly phosphorylates the two N-terminal regulatory serines within IκBα, triggering ubiquitination and rapid degradation of this inhibitor in the 26S proteasome (Bacuerle and Baltimore 1996; Baldwin 1996; Verma et al 1995). Degradation of IκBα unmasks the nuclear localization signal on NF-κB, allowing the NF-κB to translocate to the nucleus where it engages cognate κB enhancer elements and activates the transcription of various κB-dependent genes involved in inflammatory, immune, and anti-apoptotic responses.

IL-1, a second proinflammatory cytokine, acts in a manner similar to TNFα. IL-1 binding to its receptor recruits the MyD88 and TRAF-6 adapter proteins and (IRAK), a serine-threonine kinase (Cao et al 1996; Muzio et al 1997). Like TRAF-2, TRAF-6 interacts with NIK. Thus, the TNFα and IL-1 signaling pathways converge at the level of NIK. The present invention provides new insights into the molecular basis for NIK regulation of NF-κB-dependent gene expression, and provides novel methods for modulating NF-κB-dependent immune, inflammatory, and anti-apoptotic responses.

SUMMARY OF THE INVENTION

The present invention provides a molecular mechanism to interfere with cytokine induction of NF-κB-dependent immune, inflammatory, and anti apoptotic responses, through interference with the assembly of NIK and the IKK proteins. A relatively small region of NIK selectively impairs the NIK-IKK interaction. The present invention provides a novel and highly specific method for modulating NF-κB-dependent immune and inflammatory responses, based on interruption of the critical protein—protein interaction of NIK and IKK. The present invention provides methods for inhibiting NF-κB-dependent gene expression, using mutant NIK proteins. One embodiment of the present invention provides kinase-deficient NIK mutant proteins that inhibit activation of IKK. Another embodiment of the invention provides N-terminus NIK mutant proteins that bind IKK, thus inhibiting NIK/IKK interaction.

BRIEF DESCRIPTION OF THE FIGURES

FIG. 2: A) Alignment of the amino acid sequences of the activation loop between subdomains VII (DFG) and VIII (M(A/S)PE) of NIK (SEQ ID NO.: 3) and other MAP kinases, including MEKK1 (SEQ ID NO.: 4), MEKK2 (SEQ ID NO.: 5), MEKK3 (SEQ ID NO.: 6) MEK1 (SEQ ID NO.: 7), MEK2 (SEQ ID NO. 8), MEK3 (SEQ ID NO.: 9) and SEK1 (SEQ ID NO.: 10). Asterisks denote residues shown to be phosphorylated and/or implicated in the activation of these kinases. B) Biological function of wild-type NIK and kinase domain mutant forms of NIK. C) in vivo phosphorylation of wild-type NIK and the mutant forms of NIK.

FIG. 3: A) The NIK-T559A mutant protein fails to activate IKKα- and kinase activity. B) The NIK-T559A mutant protein fails to induce κB-luciferase activity. C) The expression of NIK-T559A mutant protein dominantly interferes with TNFα-induced NF-κB activation in a dose-related manner.

FIG. 5: A) Biologically active NIK spontaneously forms homotypic oligomers in vivo. B) Myc-NIK and NIK-T7 proteins are expressed at comparable levels in transfected cultures.

FIG. 8: A) All the deletion forms of Myc-NIK are comparably expressed when cotransfected with T7-IKKα. B) The C-terminus of NIK mediates heterotypic oligomerization with IKKα.

FIG. 9: A) Expression of the C-terminal 213 amino acid segment of NIK interrupts the assembly of NIK and IKKα. B) Myc-NIK and the Myc-N1–200 and Myc-N735–947 peptides are comparably expressed in transfected cultures.

FIG. 10: The amino acid and nucleic acid sequences of NIK.

DETAILED DESCRIPTION OF THE INVENTION

Terminology

Figure 1:
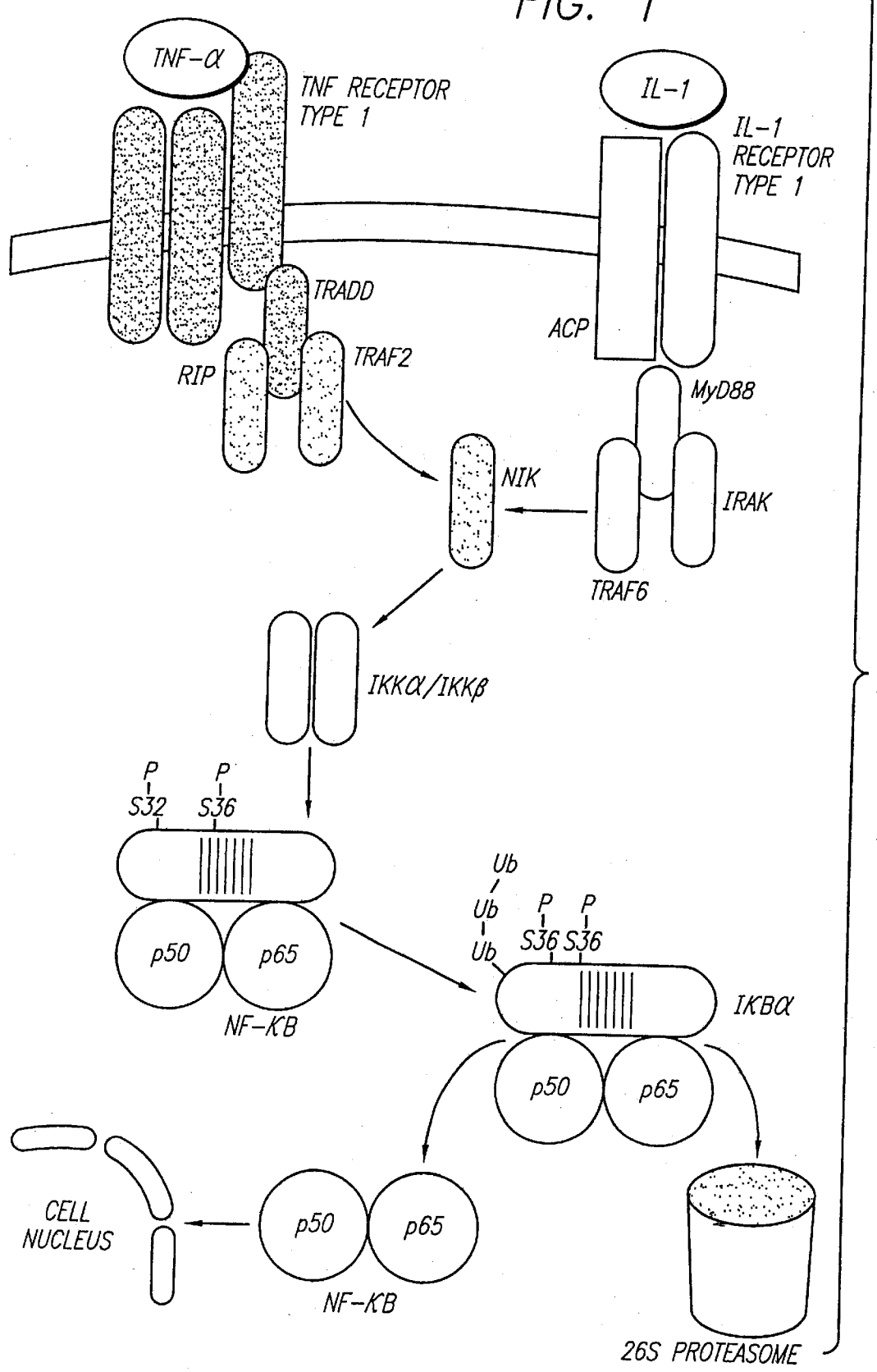
FIG. 1: Schematic summary of the overlapping and unique intracellular signaling pathways including adapter molecules and specific kinases activated by the proinflammatory cytokines TNFα and IL-1.

The term "NIK" used herein is defined as a wild-type NF-κB inducing kinase having serine/threonine kinase activity, and having the amino acid sequence as described in FIG. 10 and SEQ ID NO.: 1.

The term "mutant NIK" used herein is defined as a NIK protein that inhibits activation of NF-κB-dependent gene expression. Two categories of mutant NIK proteins are described in the present invention and are further defined below.

The term "N-terminus deletion mutant of NIK" used herein is defined as a NIK protein lacking the N-terminus and having at least the C-terminus section that interacts with IKK protein. The N-terminus deletion mutant of NIK includes N-terminus truncation mutants of NIK, and C-terminal NIK peptides that interact with IKK protein. These mutant NIK proteins may or may not retain the catalytic kinase domain of NIK. Specific examples include, but are not limited to, the following N-terminus deletion mutants of NIK: (see FIG. 10 for amino acid sequence of NIK): N350–947 (includes amino acids His350 through Pro947), N570–947 (includes amino acids Gly570 through Pro947), N624–947 (includes amino acids Pro624 through Pro 947), N735–947 (includes amino acids Glu735 through Pro947), N735–813 (includes amino acids Glu735 through Pro813), N814–947 (includes amino acids Ser814 through Pro947), and N847–947 (includes Ala847 through Pro947).

The term "kinase-deficient mutant of NIK protein" used herein is defined as a mutant NIK protein that does not exhibit catalytic kinase activity. The terms "catalytically inactive", "biologically inactive", and "kinase-deficient" define a NIK protein that does not undergo auto- or trans-phosphorylation. Such phosphorylation may involve either inter- or intra-molecular phosphorylation of the activation loop of NIK which corresponds to amino acids 534–566 which controls phosphorylation activity of NIK. Additionally, the kinase-deficient mutant NIK protein does not activate IKK. The kinase-deficient phenotype of this mutant NIK protein may be due to mutations that occur within the so-called activation loop of NIK. Specific examples include, but are not limited to, the following kinase-deficient NIK mutants: a mutant NIK protein that has three amino acid substitutions Ser-549, Thr-552, and Thr-559 all replaced with alanine residues (NIKSTT549/552/559AAA); or a mutant NIK protein that has Threonine-559 substituted with alanine (NIK-T559A). A second type of kinase deficient mutant of NIK corresponds to a mutant NIK protein that has Lys-429 and Lys-430 replaced with alanine residues (NIK-KK429/430AA). This mutant is altered at the ATP binding site of the kinase and consequently cannot mediate phosphorylation.

The term "IKK" used herein is defined as the Iκ-B-specific kinases, IKKα and IKKβ.

The term "activation of an IKK protein" used herein is defined as changing an inactive IKK protein into an IKK protein that is an IκB kinase. The activated IKK phosphorylates serine 32 and serine 36 of IκB which marks this inhibitor for ubiquitination and degradation.

The term "NIK/IKK" interaction used herein is defined as NIK/IKK protein binding, a NIK/IKK protein complex and NIK/IKK protein assembly.

The term "inhibition of NIK/IKK interaction" used herein is defined as inhibiting either the formation of a NIK/IKK protein complex or disruption of a formed NIK/IKK protein complex.

The term "NF-κB" used herein is defined as a ubiquitously expressed family of eukaryotic transcription factors, comprising a homo- or hetero-dimer of DNA-binding proteins related to the proto-oncogene c-Rel, that controls the expression of many κB-dependent immmune, inflammatory, and anti-apoptotic response genes.

The term "NF-κB-dependent gene expression" used herein is defined as those immune and inflammatory genes that are under the regulatory control of the κB-enhancer. In most cells, NF-κB exists in a latent state in the cytoplasm bound to inhibitory proteins, collectively called IκB, that mask the nuclear localization signal thereby preventing nuclear translocation. The latent form of NF-κB can be induced by cytokines, such as TNFα and IL-1. Both TNFα and IL-1 signaling leads to sequential phosphorylation and activation of a series of proteins involved in a cascade pathway that requires NIK/IKK protein interaction and IKK activation, that in turn leads to phosphorylation and degradation of IκB. Degradation of the IκB inhibitor unmasks the nuclear localization signal of the NF-κB complex allowing its rapid translocation into the nucleus where it engages cognate κB-enhancer elements and activates the transcription of various NF-κB-dependent genes involved in inflammation and immune response.

Mutant NIK

The present invention provides mutant NIK proteins. In one embodiment, the NIK mutant protein is an N-terminus deletion mutant of NIK or a C-terminal NIK peptide that has at least the C-terminus section of NIK which binds to an IKK protein. The N-terminus deletion mutant NIK protein or the C-terminal NIK peptide can have some but not all of the N-terminus section. The N-terminus deletion mutant NIK protein or the C-terminal NIK peptide can also have the central sections of NIK. But the N-terminal deletion mutant NIK protein or the C-terminal NIK peptide must have at least the C-terminus section of NIK that binds to the IKK protein. In particular, one embodiment provides an N-terminus deletion mutant NIK protein or a C-terminal NIK peptide that has an amino acid sequence beginning with glutamic acid at position 735 and ending with proline at position 947 of the wild-type NIK sequence; in the present invention, this mutant is called N735–947. The present invention is not limited to only the N-terminus deletion mutant NIK protein N735–947, as the present invention also provides for other N-terminus deletion mutant proteins that create a mutant NIK protein that can interact with an IKK protein.

In another embodiment the NIK mutant protein is a kinase deficient mutant NIK protein. The kinase deficient mutant phenotype includes a NIK protein that does not undergo auto- or trans-phosphorylation. The kinase deficient phenotype also includes a NIK protein that does not phosphorylate or activate an IKK protein. Normally, a kinase-active NIK protein will phosphorylate an IKK protein which activates the IKK protein to become an IκB kinase. Therefore, an activated IKK is an IκB kinase. The present invention provides two kinase deficient mutant NIK protein sequences that differ from the wild-type NIK protein sequence. In particular, one of the kinase deficient mutant NIK proteins has the amino acid residue threonine-559 substituted with an alanine residue; in the present invention, this mutant is called NIK-T559A. A second kinase deficient NIK mutant has three amino acid residues substituted: the amino acid residues serine-549, and threonine-552, and threonine-559 are each substituted with alanine; in the present invention, this mutant is called NIK-SST549/552/559AAA. And another kinase deficient NIK mutant has two amino acid substitutions, with lysine-429 and lysine-430 substituted with an alanine residue; in the present invention, this mutant is called NIK-KK429/430AA. The present invention is not limited to only the kinase deficient NIK mutants listed above, as the present invention also provides for other amino acid substitutions that create a mutant NIK protein that has the kinase deficient phenotype.

The invention further provides nucleic acid molecules encoding the mutant NIK proteins of the present invention. In one embodiment, the nucleic acid is cDNA. Further, the invention provides a vector, which comprises the nucleic acid molecule of the present invention. Additionally, the invention provides a host vector system. This comprises the vector of the invention in a suitable host cell, e.g., a bacterial cell or eukaryotic cell.

The invention also provides methods for producing the mutant NIK proteins of the present invention. This comprises culturing the host vector system of the invention under suitable culture conditions so as to produce the mutant NIK protein in the host and recovering the mutant NIK protein so produced. The present invention also provides mutant NIK proteins produced by the method above.

The invention provides mutant NIK proteins that are labeled with a detectable marker or conjugated to a second molecule, such as a membrane permeable agent or detectable marker, and used for targeting the second molecule to NIK's target, e.g., IKK. Suitable detectable markers include, but are not limited to, a fluorescent compound, a bioluminescent compound, and chemiluminescent compound.

Methods of the Invention

Activation of NF-κB-dependent gene expression is associated with NIK/IKK interaction and activation of IKK by NIK. The invention provides methods for inhibiting activation of NF-κB-dependent gene expression, by inhibiting the NIK/IKK interaction or by inhibiting the activation of IKK by NIK, using the mutant NIK proteins of the present invention.

One embodiment of the invention provides a method for inhibiting activation of NF-κB-dependent gene expression by inhibiting NIK/IKK interaction, by contacting an IKK protein with a catalytically inactive NIK protein that continues to interact with and bind to IKK. The inhibition of the NIK/IKK interaction includes inhibiting the formation of a NIK/IKK complex, or disruption of a formed NIK/IKK complex. One particular embodiment of the present invention provides a method for inhibiting activation of NF-κB-dependent gene expression by inhibiting wild type NIK/IKK interaction, by contacting the wild type IKK/NIK protein complex with a catalytically inactive or mutant NIK protein, such that the mutant NIK competes with the wild type NIK for assembly with the IKK, thereby forming an inactive NIK/IKK protein complex. One embodiment provides using an N-terminus deletion mutant NIK protein, such as N735–947, to inhibit NIK/IKK interaction. These N-terminus mutant NIK proteins bind to IKK protein and inhibit wild type NIK/IKK interaction, thereby inhibiting activation of NF-κB-dependent gene expression. The methods of the present invention are not limited to using only the N-terminus deletion mutant NIK protein N735–947, as the present invention also provides for use of other N-terminus deletion mutant NIK proteins and other types of NIK mutant proteins that can interact with an IKK protein to inhibit activation of NF-κB-dependent gene expression.

One embodiment of the invention provides a method for inhibiting activation of NF-κB-dependent gene expression, by using a kinase-deficient NIK mutant protein. The kinase deficient phenotype includes a NIK protein that does not undergo auto- or transphosphorylation. The kinase deficient phenotype also includes a NIK protein that does not phosphorylate or activate an IKK protein. Normally, a kinase-active NIK protein will phosphorylate an IKK protein thereby activating the IKK protein to become an IκB kinase. Therefore, an activated IKK is an IκB kinase. In particular, the present invention uses NIK proteins that have the kinase deficient phenotype, such as NIK-SST549/552/559AAA or NIK-T559A to inhibit activation of NF-κB-dependent gene expression. The methods of the present invention are not limited to using only the kinase deficient NIK mutants listed above, as the present invention also provides for other mutant NIK proteins that have the kinase deficient phenotype.

The following examples are presented to illustrate the present invention and to assist one of ordinary skill in making and using the same. The examples are not intended in any way to otherwise limit the scope of the invention.

EXAMPLE 1

Analysis of Kinase-Defective Mutants of NIK

NIK protein is a member of the family of mitogen activated protein kinase kinase kinases (MAP3Ks). Three amino acid residues located within the activation loop of the NIK kinase domain are highly conserved among MAP3Ks (Alessi et al 1994; Siow et al 1997; Yan and Templeton 1994; Zheng and K. L. Guan 1994). These amino acid residues correspond to Ser-549, Thr-552 and Thr-559 in the NIK sequence (FIG. 2A). A mutant NIK, called NIK-SST549/552/559AAA, was generated in which Ser-549, Thr-552 and Thr-559 were replaced with alanine residues. A second NIK mutant, called NIK-KK429/430AA, was altered at the ATP binding site of the NIK kinase domain. These mutant NIKs and wild-type NIK were compared for their ability to stimulate κB-dependent luciferase reporter activity in transfected human 293 embryonic kidney cells (see Material and Methods section for details of transfection method).

The results demonstrated that wild-type NIK strongly stimulated luciferase activity (FIG. 2B, closed bars). Additional stimulation of these cultures with TNFα (FIG. 2B, open bars) only weakly augmented the κB-luciferase activity, suggesting that the ectopically expressed NIK was almost fully induced. In contrast, the NIK mutants NIK-SST549/552/559AAA and NIK-KK429/430AA displayed very little spontaneous functional activity (FIG. 2B, closed bars), and both mutant NIKs functioned as dominant-negative inhibitors effectively blocking NF-κB activation induced by either TNFα or wild-type NIK FIG. 2B, open bars).

To further explore the molecular basis for NIK activation, in vivo phosphorylation of wild-type and inactive mutant NIK proteins were compared by metabolic radiolabeling with $^{32}$P-labeled orthophosphoric acid. The radiolabeling procedure described in Material and methods section was used, except that after radiolabeling for 2 hours, cells were cultured in medium either in the presence or the absence of TNFα (20 ng/ml) for 15 minutes, and then NIK was immunoprecipitated with anti-Myc antibodies.

The results demonstrated significant in vivo phosphorylation of wild-type NIK but sharply diminished phosphorylation of the biologically inactive NIK-KK429/430AA and NIK-SST549/552/559AAA (FIG. 2C, top). Addition of TNFα did not enhance the level of phosphorylation of wild-type of mutant NIKs (FIG. 2C, lanes 4 through 6). The observed decrease in phosphorylation of the two mutant NIKs was not explained by marked instability of these proteins, since immunoblotting revealed only slightly lower levels of expression for each (FIG. 2C, bottom) and the half-lives of the mutant NIK proteins is similar to that of wild-type NIK.

Together, these results show that NIK induction of NF-κB correlates with its ability to undergo auto- or trans-phosphorylation in vivo. Furthermore, phosphorylation likely involves either inter- or intra-molecular phosphorylation of the activation loop of NIK. Thus, the NIK mutants NIK-KK429/430AA and NIK-SST549/552/559AAA are kinase-deficient NIK mutants.

EXAMPLE 2
Threonine 559 Plays a Critical Role in the Regulation of NIK Function

To further determine which serine or threonine residue in the activation loop of NIK (e.g. amino acids 534–566, see FIG. 2A) is critical for the regulation of its function, a set of individual mutant NIK proteins were generated. These mutant NIK proteins contained alanine substituted for either a key conserved serine or threonine residues in this loop: NIK-S549A, NIK-T552A and NIK-T559A. These mutant NIK proteins were transfected into 293 cells and evaluated for their ability to activate the downstream kinase IKKα, and to induce NF-κB-dependent transcription.

293 cells were transfected according to the procedure described in Material and methods section below. 20 hours after transfection, in vitro kinase reactions were performed by using anti-IKKβ immunoprecipitates prepared from these cell lysates (FIG. 3A). GST-IκBα (1–62) was added as an exogenous substrate. The kinase reactions were analyzed by SDS-PAGE, followed by transfer to a nitrocellulose membrane and autoradiography. The phosphorylated GST-IκBα substrate is indicated on the right of FIG. 3A. The lower panels show the amounts of immunoprecipitated IKKα and expressed NIK present in each of the cell lysates.

For the functional assays, 293 cells were co-transfected (see Material and methods section below) with 200 ng of κB-luciferase and 100 ng of β-galactosidase reporter plasmids (6RZ), together with 1 μg of expression vector (pRK6) containing either wild-type NIK or mutant NIK-SST549/552/559/AAA, NIK-S549A, NIK-T552A or NIK-T59A. All transfections included the 6RZ plasmid to normalize for differences in gene transfer efficiency by assay of β-galactosidase activity. Twenty hours after transfection, the cultures were stimulated with or without TNFα (20 ng/ml) for 6 hours. Cell lysates were prepared from the cultures, and the luciferase activity present in these lysates was determined as described in Material and methods section below.

The results show that mutants NIK-S549A and NIK-T552A functioned similarly to wild-type NIK. However, the mutant NIK-T559A failed to induce IKKα activity (FIG. 3A) or κB-luciferase activity (FIG. 3B).

Figure 4B:
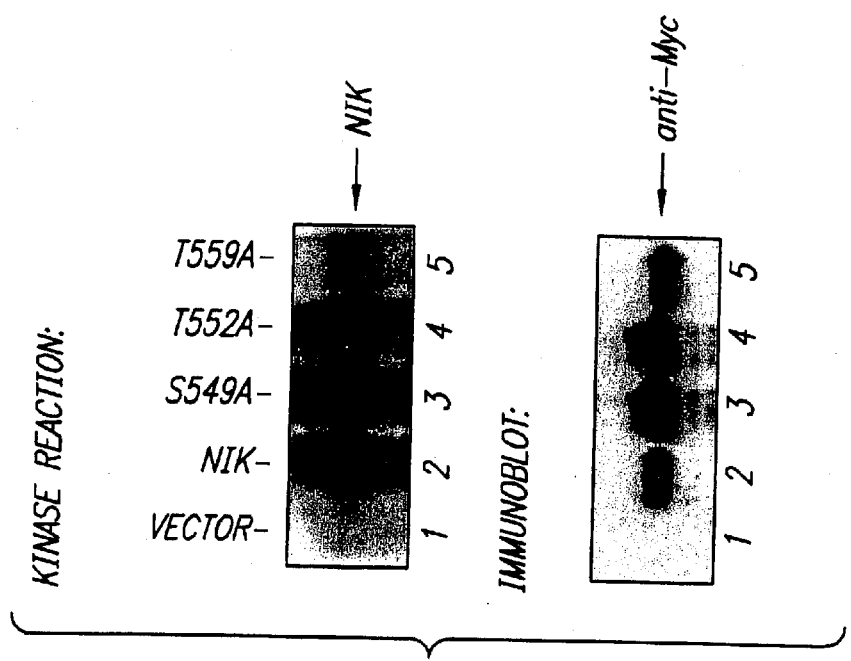
FIG. 4: A) The NIK-T559A mutant protein assembles with IKKα but fails to phosphorylate coimmunoprecipitated IKKα. B) the NIK-T559A mutant protein fails to undergo auto phosphorylation.
Figure 4A:
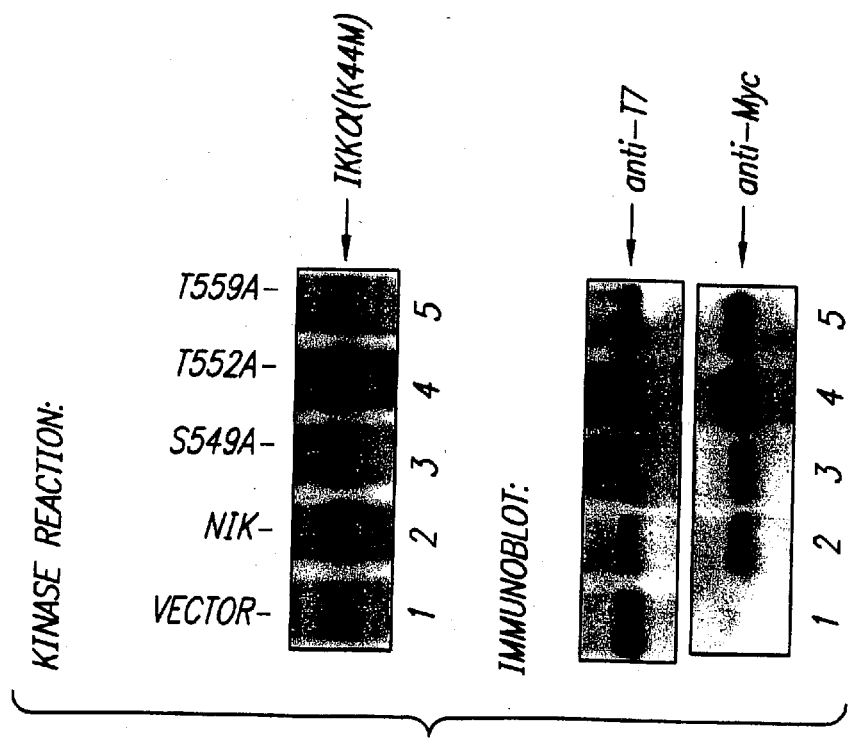

To determine whether the inability of the NIK-T559A mutant protein to activate IKKα and NF-κB-dependent transcription was due to its failure to phosphorylate IKKα, vectors encoding kinase-deficient IKKα (K44M) were co-transfected with vectors encoding wild type NIK or the inactive T559A mutant of NIK (FIG. 4A). Then, IKKα was immunoprecipitated and subjected to an immunocomplex kinase reaction to test the ability of co-immunoprecipitated NIK to phosphorylate IKKα.

The results demonstrated that wild-type NIK and mutant NIK-S549A and NIK-T552A effectively phosphorylated the coimmunoprecipitated IKKα (K44M) protein in vitro (FIG. 4A). In contrast, the mutant NIK-T559A assembled normally with IKKα (FIG. 3A, bottom) but failed to phosphorylate the coprecipitating IKKα (FIG. 4A, lane 5). In addition, NIK-T559A also lacks the ability for autophosphorylation compared to the other NIK activation loop mutant proteins (FIG. 4B, lane 5).

Together, these results show that Thr-559 corresponds to a key regulatory residue within the activation loop of NIK that is essential for NIK function. Thus, NIK-T559A is a kinase-deficient NIK mutant protein.

EXAMPLE 3
Ectopically Expressed NIK Spontaneously Forms Homotypic Oligomers in Vivo To determine if expressed NIK exists as monomeric or assembled homotypic oligomers in vivo, two different epitope-tagged versions of NIK, Myc-NIK and NIK-T7, were cotransfected into HeLa cells. Lysates from these transfected cells were then sequentially immunoprecipitated with anti-T7 antibodies and immunoblotted with anti-Myc antibodies.

HeLa cells were transiently transfected with plasmids encoding T7- and Myc-epitope-tagged versions of NIK, as described later in Material and Methods. After 24 hours of culture, a portion of the cells were treated with TNFα for 5 or 10 minutes, as indicated in FIG. 5A. Cell lysates were prepared from the cultures and subjected to immunoprecipitation (IP) with anti-T7 antibody conjugated to agarose beads. The immunoprecipitates were then analyzed by immunoblotting with anti-Myc antibodies. Aliquots of the whole-cell lysates (10 μl) were subjected to SDS-PAGE and immunoblotted with anti-T7 or anti-Myc antibodies to determine the levels of Myc-NIK and NIK-T7 expression. In addition, the biological activity of the added TNFα was confirmed by induced degradation of endogenous IκBα detected by immunoblotting with antibodies specific for the C-terminus of IκBα.

The results demonstrated that, when NIK-T7 and Myc-NIK were coexpressed, the two proteins were effectively coimmunoprecipitated (FIG. 5A, lane 2). In addition, stimulation of these cultures for 5 or 10 minutes with TNFα did not further enhance NIK oligomerization (FIG. 5A, lanes 3 and 4). However, the added TNFα was biologically active, since it induce the partial degradation of endogenous IκBα observed at 10 minutes (FIG. 5B). The immunoblotting results demonstrated that the Myc-NIK and NIK-T7 protein were expressed at comparable levels in the transfected cultures (FIG. 5B, lane 2).

Collectively, these results show that biologically active NIK forms dimers or higher order oligomers in vivo.

EXAMPLE 4

Mapping the NIK Domains Involved in Homotypic Oligomerization

Figure 6A:
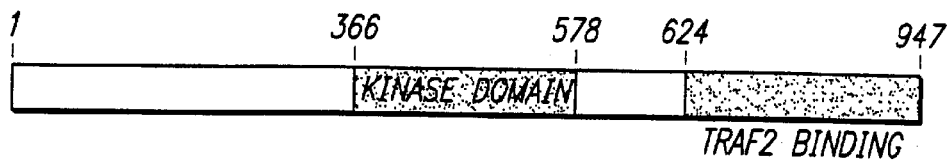
FIG. 6: A) Schematic overview of the structural organization of NIK protein. B) Myc-NIK is stably expressed in transfected 293 cells. C) Multiple domains of NIK participate in homotypic oligomerization.
Figure 6B:
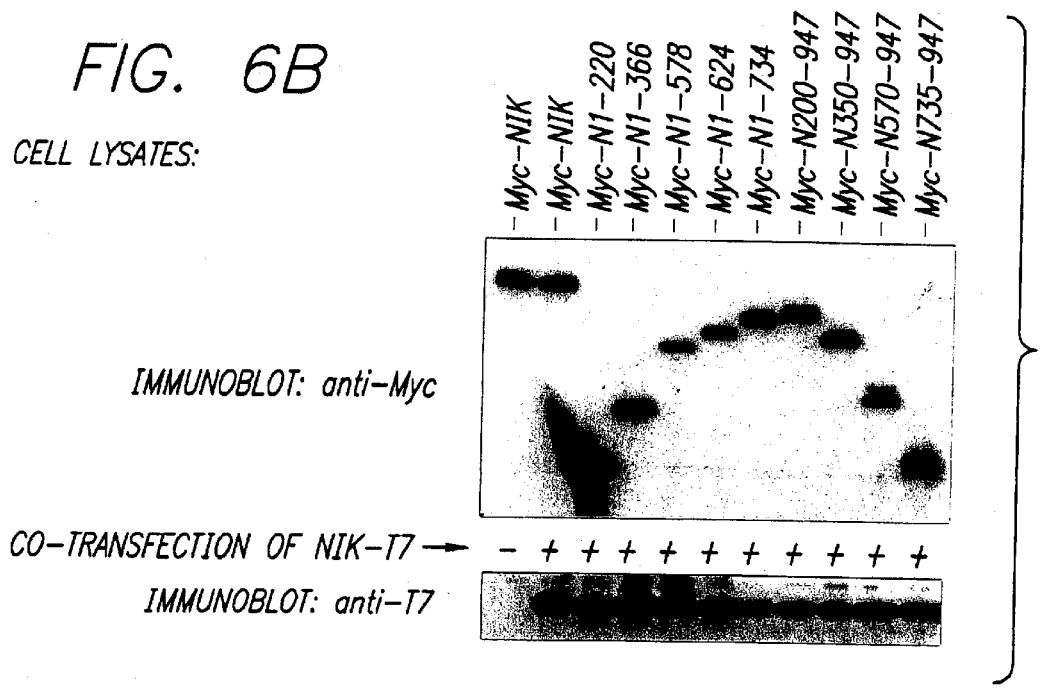

To determine which subregions of NIK mediate the homotypic interaction, a series of nested deletion mutant forms of NIK protein were prepared and tested. Each of the deletion mutant NIKs contained an N-terminal Myc epitope tag, and each was stably expressed in 293 cells cotransfected with NIK-T7 (FIG. 6B, lanes 3–11). Cell lysates were immunoblotted with anti-Myc and anti-T7 to verify protein expression levels.

24 hours after transfection, cell lysates were prepared, subjected to SDS-PAGE, and blotted with anti-Myc or anti-T7 antibodies to determine protein expression levels (FIG. 6B). To detect the presence of oligomers formed between mutant NIK proteins and NIK-T7, aliquots of cell lysates were subjected to immunoprecipitation (IP) with anti-T7 antibody conjugated to agarose beads. The immunoprecipitates were subjected to SDS-PAGE and immunoblotted with anti-Myc antibodies (FIG. 6C).

Figure 6C:
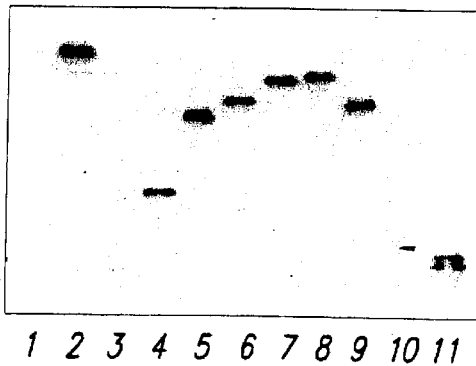

The results demonstrated that, with the exception of Myc-N1–200 and Myc-N570–947, the deletion mutant forms of NIK protein formed oligomers with NIK-T7, as indicated by their coimmunoprecipitation with anti-T7 antibodies (FIG. 6C, lanes 2–11). The results also demonstrated that NIK amino acid residues 570 to 974 failed to oligomerize, although a shorter NIK fragment containing amino acid residues 735 to 947 did form oligomers. It is possible that the 570–947 NIK fragment has an altered protein conformation due to the presence of multiple proline residues between 672 and 759.

EXAMPLE 5

Functional Effects of the C-Terminus of NIK on TNFα and Wild-Type NIK-Induced NF-κB Activation To determine the intrinsic biological function of deletion mutant forms of NIK proteins and their effects on TNF-α and NIK activation of NF-κB, 293 cells were cotransfected with a NIK deletion mutant and the κB luciferase reporter plasmid, using the method described in the Material and Methods section below. Briefly, 3 µg of expression vectors encoding a NIK deletion mutant was cotransfected into 293 cells, together with κB-luciferase and β-galactosidase reporter plasmids. 20 hours after transfection, the cultures were stimulated with or without TNFα (20 ng/ml) (FIG. 7A) or 0.3 µg of a wild-type NIK expression vector (FIG. 7B) for 6 hours (TNFα induction) or 24 hours (wild-type NIK induction). Cell lysates were prepared and the luciferase activities of these lysates were determined.

Figure 7A:
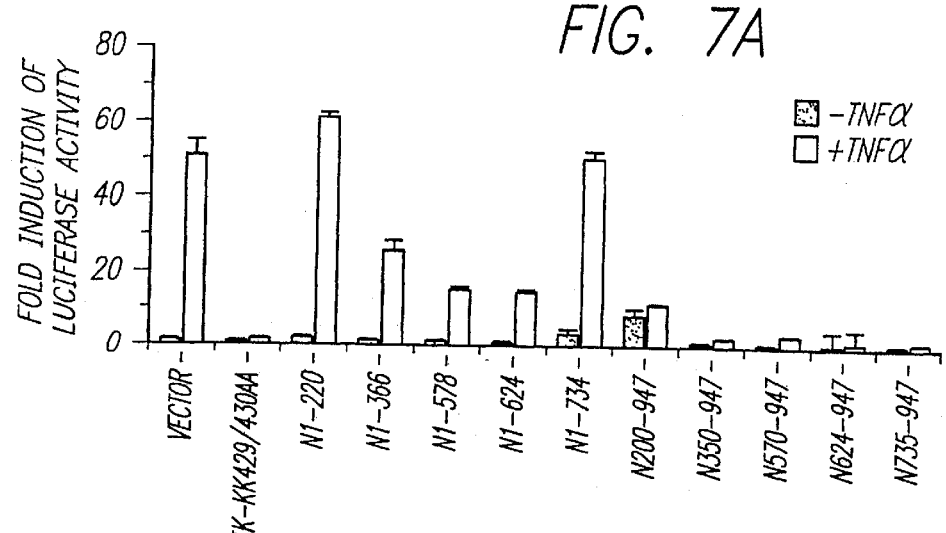
FIG. 7: A) Analysis of the functional effects of various deletion mutant forms of NIK in the presence and absence of TNFα. B) Analysis of the functional effects of various deletion mutant forms of NIK in the presence and absence of wild-type NIK protein. C) Analysis of the inhibitory effect of the C-terminus of NIK (amino acid residues 735 to 947) and shorter fragments (735–813, 814–947, 847–947) on TNFα (left graph) and NIK (right graph) induction of κB-luciferase activity.
Figure 7B:
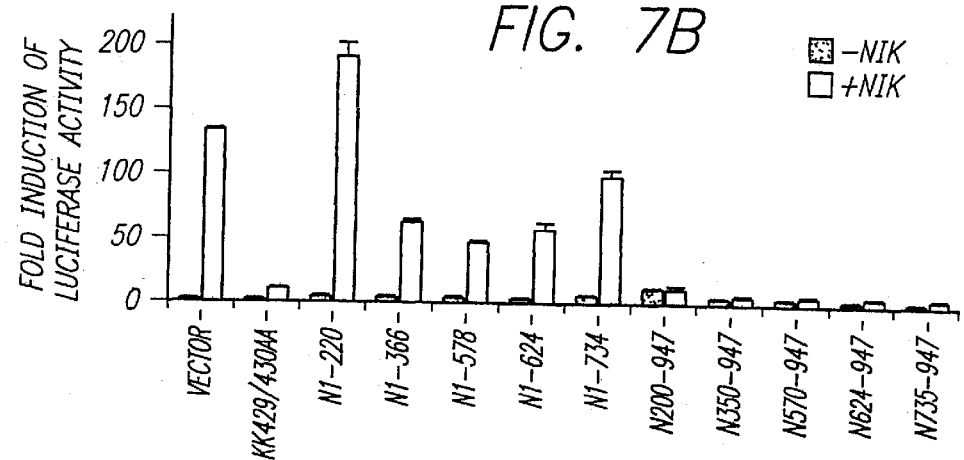

The results demonstrated that only the N200–947 mutant form of NIK retained significant, albeit weak, stimulatory activity, in the absence of induction from TNFα or wild-type NIK (FIGS. 7A and B, closed bars). When tested in the presence of TNF-α or wild type NIK as an inducer, the C-terminal deletion mutant forms of NIK (N1–366, N1–578 and N1–624) produced only modest and various degrees of inhibition (FIGS. 7A and B, open bars). In contrast, each of the N-terminus deletion mutant forms of NIK (N350–947, N578–947, N624–947 and N735–947) markedly inhibited both TNF-α and wild-type NIK induction of κB-luciferase activity.

These results confirm and extend previous studies (Malinin et al 1997) that showed residues 624 to 947 of NIK exert inhibitory effects on TNF-α signaling. Malinin previously showed that TRAF-2 interaction with NIK involves C-terminal sequences located between amino acids 624 and 947. The results presented here show that NIK interaction with IKKα similarly involves the C-terminus of NIK, specifically, an overlapping subregion encompassing residues 735 to 947.

Figure 7C:
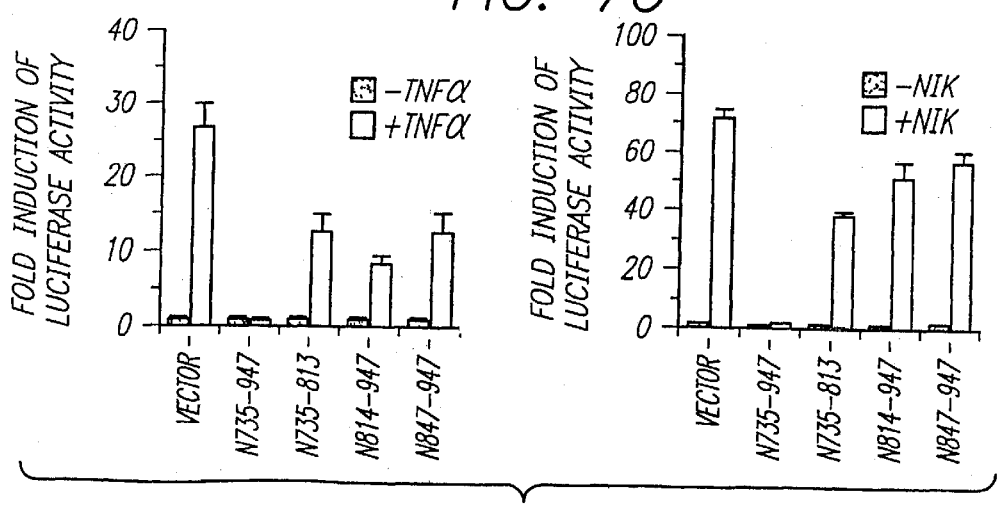

To determine which sequences of the 213-amino acid C-terminal region of NIK are required for inhibition of κB-activity, additional N-terminus deletion mutant forms of NIK (N735–813, N814–947 and N847–947) were prepared and analyzed for their ability to induce κB-luciferase expression (FIG. 7C). The co-transfection and induction methods used for this experiment are described for FIGS. 7A and B above.

The results demonstrated that none of the smaller C-terminal fragments of NIK induced an increase in κB-luciferase activity when added alone (FIG. 7C). Furthermore, none of the smaller C-terminal fragments exerted potent inhibitory effects on TNF-α-induced (FIG. 7C, left graph) or on wild type NIK-induced NF-κB-driven luciferase activity (FIG. 7C, right graph).

Thus a 213 amino acid fragment of NIK, containing the carboxyl terminus of NIK including amino acids 735 to 947, represents the smallest fragment thus far identified which potently inhibits TNF-α mediated activation on NF-κB.

EXAMPLE 6

The C-Terminus of NIK Mediates Binding to IKKα, the IκB-Specific Kinase

To further explore the biological basis for the significant inhibitory effects of the C-terminal region of NIK (N735–947) on TNF-α signaling, the potential role of this region in NIK binding to IKKα was examined.

IKKα-T7 was coexpressed with the various Myc-NIK deletion mutants followed by coimmunoprecipitation with anti-T7 antibodies and immunoblotting with anti-Myc antibodies (FIG. 8). In this experiment, the kinase-deficient mutant, NIK-KK429/430AA (see Example 1, FIG. 2B), was used in place of the wild-type NIK to avoid potential phosphorylation of IKKα which might weaken the NIK-IKKα interaction. 293 cells were cotransfected with IKKα-T7 and Myc-NIK or a deletion form of NIK (Myc-NIK), using the method described in Material and Methods section below. Briefly, the immunoblotting experiment was performed as follows. 24 hours after transfection, cell lysates were prepared, subjected to SDS-PAGE, and immunoblotted with anti-Myc antibodies or anti-T7 antibodies to determine the overall level of expression of the individual proteins (FIG. 8A). Aliquots of the cell lysates were subjected to immunoprecipitation (IP) with anti-T7 antibodies conjugated to agarose beads. The immunoprecipitates were then subjected to SDS-PAGE and immunoblotted with anti-Myc antibodies (FIG. 8B).

The results demonstrated that all of the deletion mutant forms of NIK and T7-IKKα were comparably expressed in these transfection experiments (FIG. 8A). The results also demonstrated that the kinase-deficient NIK mutant (Myc-NIK-KK429/430A) interacts with IKKα, as shown by the coimmunoprecipitation results (FIG. 8B, lane 2). Furthermore, the results demonstrated that none of the C-terminus deletion mutant forms of NIK assembled with IKKα (FIG. 8B, lanes 3–7), while all of the N-terminus deletion mutant proteins, including N735–947, effectively associated with IKKα (FIG. 8B, lanes 8–11).

EXAMPLE 7
Expression of the C-Terminal 213-Amino-Acid Segment of NIK Interrupts the Assembly of NIK and IKKα

To determine if expression of the 213-amino-acid C-terminal fragment of NIK (N735–947) is sufficient to disrupt the interaction of NIK and IKKα, cells were cotransfected with Myc-NIK and IKKα-T7, and with either Myc-N735–947 or Myc-N1–220. The Myc-N1–220 construct expresses a comparably-sized peptide containing the N-terminus of NIK (residues 1 to 220), and was used as a control in this experiment. 293 cells were cotransfected using the method described in the Material and Methods section below. Briefly, the immunoblotting experiment was performed as follows. 24 hours after transfection, cell lysates were prepared from the transfected cultures. Aliquots of the cell lysates were subjected to immunoprecipitation (IP) with anti-T7 antibodies conjugated to agarose beads. The immunoprecipitates were then subjected to SDS-PAGE and immunoblotted with anti-Myc antibodies (FIG. 9A). Aliquots of the cell lysates were subjected to SDS-PAGE and immunoblotted with anti-Myc antibodies to assess the expression of the individual proteins (FIG. 9B).

The results demonstrated that the N-terminus deletion NIK mutant, containing NIK residues 735 through 947 (Myc-N735–947) effectively blocked the physical association of IKKα (IKKα-T7) with NIK (Myc-NIK) (FIG. 9A, lane 3), since a NIK/IKKα complex did not immunoprecipitate when the N-terminal fragment of NIK was coexpressed. The results also demonstrated that full-length NIK (Myc-NIK) and the two NIK fragments (Myc-N1–220 and Myc-N735–947) were comparably expressed in these transfected cultures (FIG. 9B). Furthermore, the results demonstrated that the N-terminal fragment of NIK (Myc-N1–200) did not block NIK/IKKα association.

Collectively, the results presented in FIGS. 8 and 9 show that the C-terminus of NIK, containing amino acids 735 through 945, corresponds to a binding domain for IKKα that is both necessary and sufficient for NIK binding to IKKα. Additionally, in TNFα signaling assays, the C-terminal fragment of NIK prevents effective assembly of NIK and IKKα, resulting in inhibition of NF-κB-dependent activation.

Figure 11:
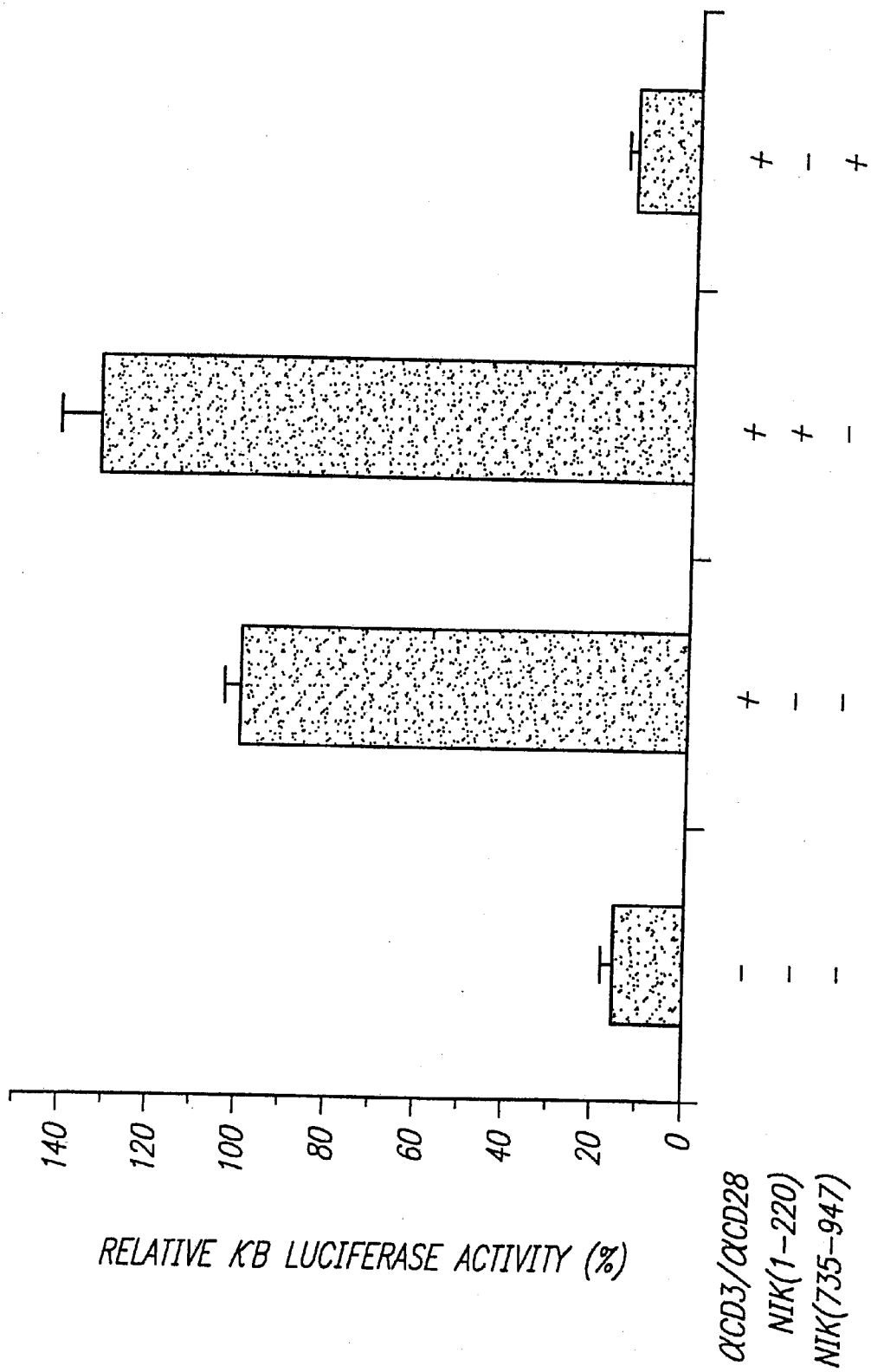
FIG. 11: κB-specific gene expression induce by anti-CD3–CD28 stimulation is inhibited by expression of the NIK (735–947) peptide but not by the NIK (1–220) peptide.

EXAMPLE 8
Expression of the C-Terminal 213 Amino Acid Segment of NIK Interrupts CD3-CD2 Costimulatory Signaling The activation of T cells requires two signals involving binding of antigen to the T cell receptor and the binding of B7 ligands to CD28 receptors on T cells. Binding of these receptors promotes the activation of L-2 gene expression which is dependent on NF-κB/c-Rel induction. Binding of these receptors includes binding of the receptor to its cognate ligand, or ligation of the receptor with antibody. Our recent studies now demonstrate that the NIK 735–947 effectively inhibits CD3–CD28 mediated co-stimulation of a composite enhancer element present in the IL-2 gene (FIG. 11). In contrast, a similarly sized N-terminal peptide, NIK 1–200, was without effect. These findings indicate that the C-terminal domain of NIK forms not only an effective inhibitor of TNFα stimulation, but also of immune activation mediated through the T cell receptor CD3 complex and the CD28 co-receptor.

Material and Methods
Expression Vector, Biological Reagents, and Cell Lines

Plasmid κB-TATA-luciferase has been previously described (S. -C. Sun et al 1996). The LacZ reporter construct containing the Rous sarcoma virus long terminal repeat (6RZ) was obtained from D. Pearce (University of California, San Fransisco).

The full-length NIK cDNA was generated in three fragments by reverse transcription-PCR using Jurkat E6-1 mRNA and three pairs of primers (see Lin et al 1998 for sequence of primers) based on the sequence published by Malinin et al (Malinin et al 1997). The PCR fragments were subcloned into pBluescript, and the full-length NIK cDNA was reconstituted by sequentially subcloning the fragments into the pRK vector (provided by Allan Hall, University College London) in frame with an N-terminal Myc epitope tag. The resulting full-length NIK cDNA was designated pRK-Myc-NIK. The full-length NIK cDNA was further subcloned into pEV3S in frame with a C-terminal T7 epitope tag and was designated pEV-NIK-T7. The two kinase domain NIK mutants, NIK-KK429/430AA and NIK-S549A/T552A/T559A, were generated by overlapping PCR. Murine IKKα/CHUK has been described previously (Connelly and Marcu 1995) and was subcloned into pEV3S in frame with a C-terminal T7 epitope to generate pEV-IKKα-T7. Recombinant human TNFα was purchased from Endogen (Cambridge, Mass.) HeLa and 293 cells were maintained in Dulbecco modified Eagle medium supplemented with 10% heat-inactivated fetal bovine serum, penicillin, and streptomycin.

Transfections and Reporter Gene Assays 293 cells ($5 \times 10^5$ cells/well) were seeded into six-well (35 mm diameter) plates and transfected the following day with 4 µg of DNA by the calcium phosphate precipitation method (Sambrook, Fritz and Maniatis 1989). Cells were co-transfected with plasmid κB-TATA-luciferase (S. -C. Sun et al 1996), the LacZ reporter construct containing the Rous sarcoma virus long terminal repeat (6RZ) (obtained from D. Pearce University of California, San Francisco), and an expression vector (pEV3S) containing wild-type or mutant NIK subcloned in-frame with a C-terminal T7 epitope tag. All transfections included the 6RZ plasmid to normalize for differences in gene transfer efficiency by assay of β-galactosidase activity. The mutant NIKs were generated by overlapping PCR. After 15 to 20 hours, selected cultures were stimulated with TNFα (20 ng/ml) for 6 hours. Luciferase activity was typically measured 20 to 25 hours after transfection using the enhanced luciferase assay kit and a Monolight 2010 luminometer (Analytical Luminescence Laboratory, Ann Arbor, Mich.). Data were presented as fold induction of luciferase activity ± the standard deviations derived from independent triplicate transfections.

Immunoprecipitation

Immunoprecipitation was performed by lysing the transfected cells 24 hours later in ELB buffer containing 1.5% Nonidet P-40, 250 mM NaCl, 50 mM HEPES (pH=7.4), 1 mM EDTA, and the following protease inhibitors: 1 mM phenylmethylsulfonyl fluoride, 5 µg/ml antipain, 5 µg/ml aprotinin, 5 µg/ml leupeptin, 0.5 µg/ml pepstatin, 7.5 µg/ml bestatin, 4 µg/ml phosphoroamidon, and 5 µg/ml trypsin inhibitor. Lysates were immunoprecipitated with anti-T7-Tag antibody linked to agarose beads (Novagen, Madison, Wis.). Immunoprecipitates were washed three times in lysis buffer and then subjected to sodium dodecyl sulfate-polyacrylamide gel electrophoresis (SDS-PAGE), followed by transfer to nitrocellulose membranes and immunoblotting with anti-Myc-Tag antibodies (Santa Cruz Biotechnology, Santa Cruz, Calif.).

Immune Complex Kinase Assays

For the immune complex kinase assays, transfected cells were lysed 12 to 18 hours post-transfection, and immunoprecipitated with antibodies and protein A-agarose beads, as described above. Immunoprecipitated beads were further washed with kinase buffer containing 10 mM HEPES (pH=

7.4), 1 mM MnCl$_2$, 5 mM MgCl$_2$, 12.5 mM β-glycero-2-phosphate, 50 μM Na$_3$VO$_4$, 2 mM NaF, and 50 μM dithiothreitol. After suspension in 20 μl of kinase buffer, the immunoprecipitates were incubated with 5 μCi of [γ-$^{32}$P] ATP (6000 Ci/mmol) with or without 1 μg of recombinant glutathione S-transferase (GST)-IκBα (1–62) as an exogenous substrate for 30 minutes at 30° C. The reaction was terminated by the addition of SDS sample buffer. The samples were analyzed by SDS-PAGE, followed by transfer to nitrocellulose membranes and exposure to Hyperfilm MP (Amersham Life Sciences). The membranes were subsequently probed with antibodies to determine the amount of immunoprecipitated quinces.

In Vivo Radiolabeling with $^{32}$P-Labeled Orthophosphoric Acid 24 hours after transfection, the cells were washed once in phosphate-free Dulbecco modified Eagle medium (Life Technologies) supplemented with 10% dialyzed, heat-inactivated fetal bovine serum and starved for 1 hour in the same medium. $^{32}$P-labeled orthophosphoric acid (0.5 mCi) was then added to the cells. After incubation for 2 hours, the cells were lysed in ELB buffer and immunoprecipitated with anti-Myc-Tag antibody and protein A-agarose as described above. Immunoprecipitates were analyzed by SDS-PAGE, followed by transfer to nitrocellulose membranes and exposure to Hyperfilm MP. Immunoblotting was performed with anti-Myc-Tag antibodies to assess the levels of immunoprecipitated NIK proteins.

REFERENCES

Alessi, D. R., Y. Saito, D. G. Campbell, P. Cohen, G. Sithandan, U. Rapp, A. Ashworth, C. J. Marshall, S. Cowley. 1994. Embo. J. 13:1610–1619.

Baeuerle, P. A. and D. Baltimore. 1996. NF-kappa B: ten years after, Cell 87:13–20

Baldwin, A. J. 1996. The NF-kappa B and I kappa B proteins: new discoveries and insights. Annu Rev Immunol 14:649–83

Brockman, J. A., D. C. Scherer, T. A. McKinsey, S. M. Hall, X. Qi, W. Y. Lee and D. W. Ballard. 1995. Coupling of a signal response domain in I kappa B alpha to multiple pathways for NF-kappa B activation. Mol Cell Biol 15:2809–18

Cao, Z., J. Xiong, M. Takeuchi, T. Kurama, and D. V. Goeddel. 1996. TRAF6 is a signal transducer for interleukin-1. Nature 383:443–6

Connelly, M. A. and K. B. Marcu. 1995. Cell Mol Biol Res 42:537–49

DiDonato, J. A., M. Hayakawa, D. M. Rothwarf, E. Zandi and M. Karin. 1997. A cytokine-responsive IkappaB kinase that activates the transcription factor NF-kappaB Nature 388:548–54

Franger, G. R., N. L. Johnson, G. L. Johnson. 1997. MEK kinases are regulated by EGF and selectively interact with Rac/Cdc42. EMBO J 16:4961–72

Good, L., and S. C. Sun. 1996. Persistent activation of NF-kappa B/Rel by human T-cell leukemia virus type 1 tax involves degradation of I kappa B beta. J Virol 70:2730–5

Hirano, M., S. Osada, T. Aoki, S. Hirai, M. Hosaka, J. Inoue and S. Ohno. 1996. MEK kinase is involved in tumor necrosis factor alpha-induced NF-kappaB activation and degradation of IkappaB-alpha. J Biol Chem 271:13234–8

Hsu, H., J. Huang, H. B. Shu, V. Baichwal and D. V. Goeddel. 1996. TNF-dependent recruitment of the protein kinase RIP to the TNF receptor-1 signaling complex. Immunity 4:387–96

Hsu, H., H. B. Shu, M. G. Pan and D. V. Goeddel. 1996. TRADD-Traf2 and TRADD-FADD interactions define two distinct TNF receptor 1 signal transduction pathways. Cell 84:299–308

Knaus, U. G., S. Morris, H. J. Dong, J. Chernoff and G. M. Bokoch. 1995. Regulation of human leukocyte p21-activated kinases through G-protein-coupled receptors. Science 269:221–3

Lee, F. S., J. Hagler, Z. J. Chen and T. Maniatis. 1997. Activation of the IkappaB alpha kinase complex by MEKK1, a kinase of the JNK pathway. Cell 88:213–22

Liu, Z. G., H. Hsu, D. V. Goeddel and M. Karin. 1996. Dissection of TNF receptor 1 effector functions: JNK activation is not linked to apoptosis while NF-kappaB activation prevents cell death. Cell 87:565–76

Malinin, N. L., M. P. Boldin, A. V. Kovalenko and D. Wallach. 1997. MAP3K-related kinase involved in NF-kappaB induction by TNF, CD95 and IL-1. Nature 385:540–4

Mercurio, F., H. Zhu, B. W. Murray, A. Shevchenko, B. L. Bennett, J. Li, D. B. Young, M. Barbosa, M. Mann, A. Manning and A. Rao. 1997. IKK-1 and IKK-2: cytokine-activated IkappaB kinases essential for NF-kappaB activation. Science 278:860–6

Muzio, M., J. Ni, P. Feng and V. M. Dixit. 1997. IRAK (Pelle) family member IRAK-2 and MyD88 as proximal mediators of IL-1 signaling. Science 278:1612–15

Perona, R., S. Montainer, L. Saniger, P. I. Sanchez, R. Bravo and J. C. Lacal. 1997. Activation of the nuclear factor-kappaB by Rho, CDC42 and Rac-1 proteins. Genes Dev 11:463–75

Regnier, C. H., H. Y. Song, X. Gao, D. V. Goeddel, Z. Cao and M. Rothe. 1997. Identification and characterization of an IkappaB kinase. Cell 90:373–83

Sambrook, Fritz and Maniatis. 1989 2$^{nd}$ edition. Molecular Cloning: A Laboratory Manual Siow Y. L., G. B. Kalmar, J. S. Sanghera, G. Tai, S. S. Oh, S. L. Pelech, 1997. J Biol Chem 272:7586–94

Smith, M. R. and W. C. Greene. 1991. Molecular biology of the type I human T-cell leukemia virus (HTLV-I) and adult T-cell leukemia. J Clin Invest 87:761–6

Song, H. Y., C. H. Regnier, C. J. Kirschning, D. V. Goeddel and M. Rothe. 1997. Tumor necrosis factor (TNF)-mediated kinase cascades: bifurcation of nuclear factor-kappaB and c-jun N-terminal kinase (JNK/SAPK) pathways at TNF receptor-associated factor 2. Proc Natl Acad Sci USA 94:9792–6

Sulciner, D. J., K. Irani, Z. X. Yu, V. J. Ferrans, C. P. Goldschmidt, T. Finkel. 1996. Rac1 regulates a cytokine-stimulated, redox-dependent pathway necessary for NF-kappaB activation. Mol Cell Biol 16:7115–21

Sun, S. C., J. Elwood, C. Beraud and W. C. Greene. 1994. Human T-cell leukemia virus type I Tax activation of NF-kappaV/Rel involves phosphorylation and degradation of I kappa B alpha and RelA (p65)-mediated induction of the c-rel gene. Mol Cell Biol 14:7377–84

Sun, S. C., J. Elwood, W. C. Greene. 1996. Mol Cell Biol 16:1058–65.

Verma, I. M., J. K. Stevenson, E. M. Schwartz, A. D. Van and S. Miyamoto. 1995. Rel/NF-kappa B/I kappa B family: intimate tales of association and dissociation. Genes Dev 9:2723–35

Woronicz, J. D., X. Gao, Z. Cao, M. Rothe and D. V. Goeddel. 1997. IkappaB kinase-beta: NF-kappaB activation and complex formation with IkappaB kinase-alpha and NIK. Science 278:866–9

Yan, M. and D. J. Templeton. 1994. J Biol Chem 269:19067–73

Zandi, E., D. M. Rothwarf, M. Delhase, M. Hayakawa and M. Karin. 1997. The IkappaB kinase complex (IKK) contains two kinase subunits, IKKalpha and IKKbeta, necessary for IkappaB phosphorylation and NF-kappaB activation. Cell 91:243–52

Zheng, C. F. and K. L. Guan. 1994. EMBO J 13:1123–31

What is claimed:

1. A method for inhibiting a first NIK/IKK protein interaction, the method comprising:
   contacting the first NIK/IKK protein complex with a mutant NIK protein that competes with the NIK of the first NIK/IKK complex so as to form a second NIK/IKK protein complex, thereby inhibiting the first NIK/IKK protein interaction.

2. The method of claim 1, wherein the mutant NIK protein is an N-terminal deletion mutant NIK protein that interacts with the IKK protein.

3. The method of claim 1 or 2 wherein the NIK protein is an N-terminus deletion mutant NIK protein, having an amino acid sequence beginning with glutamic acid at position 735 and ending with proline at position 947 of SEQ ID NO: 1.

4. A method for inhibiting activation of an endogenous IKK protein, comprising:
   contacting the endogenous IKK protein with a kinase deficient mutant NIK protein so as to form a complex, thereby inhibiting activation of the endogenous IKK protein.

5. A method for inhibiting phosphorylation of an endogenous IKK protein, the method comprising:
   contacting the endogenous IKK protein with a kinase deficient mutant NIK protein so as to from a complex, thereby inhibiting phosphorylation of the endogenous IKK protein.

6. A method for inhibiting activation of NF-κB-dependent gene expression associated with a NIK/IKK protein interaction, wherein the NIK/IKK protein interaction is inhibited by the method of claim 1.

7. A method for inhibiting activation of NF-κB-dependent gene expression associated with activation of an IKK protein, wherein activation of the IKK protein is inhibited by the method of claim 4.

8. A method for inhibiting activation of NF-κB-dependent gene expression associated with phosphorylation of an IKK protein, wherein phosphorylation of the IKK protein is inhibited by the method of claim 5.

9. A method for inhibiting a κB-dependent immune response by inhibiting activation of NF-κB-dependent gene expression associated with a NIK/IKK protein interaction, by the method of claim 6.

10. The method of claim 9, wherein the κB-dependent immune response is a κB-dependent inflammatory response.

11. The method of claim 9, wherein the κB-dependent immune response is a κB-dependent anti-apoptotic response.

\* \* \* \* \*

SEQUENCE LISTING

<160> NUMBER OF SEQ ID NOS: 10

<210> SEQ ID NO 1
<211> LENGTH: 947
<212> TYPE: PRT
<213> ORGANISM: NF-KAPPA B INDUCING KINASE (NIK)

<400> SEQUENCE: 1

```
Met Ala Val Met Glu Met Ala Cys Pro Gly Ala Pro Gly Ser Ala Val
1               5                   10                  15

Gly Gln Gln Lys Glu Leu Pro Lys Pro Lys Glu Lys Thr Pro Pro Leu
            20                  25                  30

Gly Lys Lys Gln Ser Ser Val Tyr Lys Leu Glu Ala Val Glu Lys Ser
        35                  40                  45

Pro Val Phe Cys Gly Lys Trp Glu Ile Leu Asn Asp Val Ile Thr Lys
    50                  55                  60

Gly Thr Ala Lys Glu Gly Ser Glu Ala Gly Pro Ala Ala Ile Ser Ile
65                  70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
            100                 105                 110

Ser Leu Asp Gln Ile Pro Asn Asn Val Ala His Ala Thr Glu Gly Lys
        115                 120                 125

Met Ala Arg Val Cys Trp Lys Gly Lys Arg Arg Ser Lys Ala Arg Lys
    130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Glu Ser Cys Thr Ile
                165                 170                 175

Pro Val Gln Glu Asp Glu Ser Pro Leu Gly Ala Pro Tyr Val Arg Asn
            180                 185                 190

Thr Pro Gln Phe Thr Lys Pro Leu Lys Glu Pro Gly Leu Gly Gln Leu
        195                 200                 205

Cys Phe Lys Gln Leu Gly Glu Gly Leu Arg Pro Ala Leu Pro Arg Ser
    210                 215                 220

Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
                245                 250                 255

Pro Phe Pro Tyr Ser Arg Leu Pro His Pro Phe Pro Phe His Pro Leu
            260                 265                 270

Gln Pro Trp Lys Pro His Pro Leu Glu Ser Phe Leu Gly Lys Leu Ala
        275                 280                 285

Cys Val Asp Ser Gln Lys Pro Leu Pro Asp Pro His Leu Ser Lys Leu
    290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335
```

-continued

Leu Val His Ala Leu Gln Gly Ser Val Ser Ser Gln Ala His Ser
            340                 345                 350
Leu Thr Ser Leu Ala Lys Thr Trp Ala Ala Arg Gly Ser Arg Ser Arg
            355                 360                 365
Glu Pro Ser Pro Lys Thr Glu Asp Asn Glu Gly Val Leu Leu Thr Glu
            370                 375                 380
Lys Leu Lys Pro Val Asp Tyr Glu Tyr Arg Glu Val His Trp Ala
385                 390                 395                 400
Thr His Gln Leu Arg Leu Gly Arg Gly Ser Phe Gly Glu Val His Arg
            405                 410                 415
Met Glu Asp Lys Gln Thr Gly Phe Gln Cys Ala Val Lys Lys Val Arg
            420                 425                 430
Leu Glu Val Phe Arg Ala Glu Glu Leu Met Ala Cys Ala Gly Leu Thr
            435                 440                 445
Ser Pro Arg Ile Val Pro Leu Tyr Gly Ala Val Arg Glu Gly Pro Trp
            450                 455                 460
Val Asn Ile Phe Met Glu Leu Leu Glu Gly Gly Ser Leu Gly Gln Leu
465                 470                 475                 480
Val Lys Glu Gln Gly Cys Leu Pro Glu Asp Arg Ala Leu Tyr Tyr Leu
            485                 490                 495
Gly Gln Ala Leu Glu Gly Leu Glu Tyr Leu His Ser Arg Arg Ile Leu
            500                 505                 510
His Gly Asp Val Lys Ala Asp Asn Val Leu Leu Ser Ser Asp Gly Ser
            515                 520                 525
His Ala Ala Leu Cys Asp Phe Gly His Ala Val Cys Leu Gln Pro Asp
            530                 535                 540
Gly Leu Gly Lys Ser Leu Leu Thr Gly Asp Tyr Ile Pro Gly Thr Glu
545                 550                 555                 560
Thr His Met Ala Pro Glu Val Val Leu Gly Arg Ser Cys Asp Ala Lys
            565                 570                 575
Val Asp Val Trp Ser Ser Cys Cys Met Met Leu His Met Leu Asn Gly
            580                 585                 590
Cys His Pro Trp Thr Gln Phe Phe Arg Gly Pro Leu Cys Leu Lys Ile
            595                 600                 605
Ala Ser Glu Pro Pro Val Arg Glu Ile Pro Pro Ser Cys Ala Pro
            610                 615                 620
Leu Thr Ala Gln Ala Ile Gln Glu Gly Leu Arg Lys Glu Pro Ile His
625                 630                 635                 640
Arg Val Ser Ala Ala Glu Leu Gly Gly Lys Val Asn Arg Ala Leu Gln
            645                 650                 655
Gln Val Gly Gly Leu Lys Ser Pro Trp Arg Gly Glu Tyr Lys Glu Pro
            660                 665                 670
Arg His Pro Pro Pro Asn Gln Ala Asn Tyr His Gln Thr Leu His Ala
            675                 680                 685
Gln Pro Arg Glu Leu Ser Pro Arg Ala Pro Gly Pro Arg Pro Ala Glu
            690                 695                 700
Glu Thr Thr Gly Arg Ala Pro Lys Leu Gln Pro Pro Leu Pro Pro Glu
705                 710                 715                 720
Pro Pro Glu Pro Asn Lys Ser Pro Pro Leu Thr Leu Ser Lys Glu Glu
            725                 730                 735
Ser Gly Met Trp Glu Pro Leu Pro Leu Ser Ser Leu Glu Pro Ala Pro
            740                 745                 750

```
Ala Arg Asn Pro Ser Ser Pro Glu Arg Lys Ala Thr Val Pro Glu Gln
            755                 760                 765

Glu Leu Gln Gln Leu Glu Ile Glu Leu Phe Leu Asn Ser Leu Ser Gln
    770                 775                 780

Pro Phe Ser Leu Glu Glu Gln Glu Gln Ile Leu Ser Cys Leu Ser Ile
785                 790                 795                 800

Asp Ser Leu Ser Leu Ser Asp Asp Ser Glu Lys Asn Pro Ser Lys Ala
                805                 810                 815

Ser Gln Ser Ser Arg Asp Thr Leu Ser Ser Gly Val His Ser Trp Ser
            820                 825                 830

Ser Gln Ala Glu Ala Arg Ser Ser Trp Asn Met Val Leu Ala Arg
            835                 840                 845

Gly Arg Pro Thr Asp Thr Pro Ser Tyr Phe Asn Gly Val Lys Val Gln
            850                 855                 860

Ile Gln Ser Leu Asn Gly Glu His Leu His Ile Arg Glu Phe His Arg
865                 870                 875                 880

Val Lys Val Gly Asp Ile Ala Thr Gly Ile Ser Ser Gln Ile Pro Ala
                885                 890                 895

Ala Ala Phe Ser Leu Val Thr Lys Asp Gly Gln Pro Val Arg Tyr Asp
            900                 905                 910

Met Glu Val Pro Asp Ser Gly Ile Asp Leu Gln Cys Thr Leu Ala Pro
            915                 920                 925

Asp Gly Ser Phe Ala Trp Ser Trp Arg Val Lys His Gly Gln Leu Glu
            930                 935                 940

Asn Arg Pro
945

<210> SEQ ID NO 2
<211> LENGTH: 2844
<212> TYPE: DNA
<213> ORGANISM: NF-KAPPA B INDUCING KINASE (NIK)

<400> SEQUENCE: 2
atggcagtga tggaaatggc ctgcccaggt gcccctggct cagcagtggg gcagcagaag      60
gaactcccca agccaaagga gaagacgccg ccactgggga gaaacagag ctccgtctac     120 aagcttgagg ccgtggagaa gagccctgtg ttctgcggaa agtgggagat cctgaatgac     180
gtgattacca agggcacagc caaggaaggc tccgaggcag gccagctgc catctctatc     240 atcgcccagg ctgagtgtga gaatagccaa gagttcagcc caccttttc agaacgcatt     300 ttcatcgctg gtccaaaca gtacagccag tccgagagtc ttgatcagat ccccaacaat     360
gtggcccatg ctacagaggg caaaatggcc cgtgtgtgtt ggaagggaaa gcgtcgcagc     420
aaagcccgga gaaacggaa gaagagagc tcaaagtccc tggctcatgc aggagtggcc     480
ttggccaaac ccctccccag gaccctgag caggagagc gcaccatccc agtgcaggag     540
gatgagtctc cactcggcgc cccatatgtt agaaacaccc cgcagttcac caagcctctg     600
aaggaaccag gccttgggca actctgttt aagcagcttg gcgagggcct acggccggct     660
ctgcctcgat cagaactcca caactgatc agcccttgc aatgtctgaa ccacgtgtgg     720
aaactgcacc accccagga cggaggcccc ctgcccctgc ccacgcaccc cttccctat     780 agcagactgc tcatcccctt ccattccac cctctccagc cctggaaacc tcacctctg     840 gagtccttcc tgggcaaact ggcctgtgta gacagccaga acccttgcc tgacccacac     900 ctgagcaaac tggcctgtgt agacagtcca aagcccctgc tggcccacac cctggagccc     960
```

-continued

```
agctgcctgt ctcgtggtgc ccatgagaag ttttctgtgg aggaatacct agtgcatgct    1020
ctgcaaggca gcgtgagctc aagccaggcc cacagcctga ccagcctggc caagacctgg    1080
gcagcacggg gctctagatc ccgggagccc agccccaaaa ctgaggacaa cgagggtgtc    1140
ctgctcactg agaaactcaa gccagtggat tatgagtacc gagaagaagt ccactgggcc    1200
acgcaccagc tccgcctggg cagaggctcc ttcggagagg tgcacaggat ggaggacaag    1260
cagactggct tccagtgcgc tgtcaaaaag gtgcggctgg aagtatttcg ggcagaggag    1320
ctgatggcat gtgcaggatt gacctcaccc agaattgtcc ctttgtatgg agctgtgaga    1380
gaagggcctt gggtcaacat cttcatggag ctgctggaag gtggctccct gggccagctg    1440
gtcaaggagc agggctgtct cccagaggac cgggccctgt actacctggg ccaggccctg    1500
gagggtctgg aatacctcca ctcacgaagg attctgcatg gggacgtcaa agctgacaac    1560
gtgctcctgt ccagcgatgg gagccacgca gccctgtgt acttttggcca tgctgtgtgt    1620 cttcaacctg atggcctggg aaagtccttg ctcacagggg actacatccc tggcacagag    1680
acccacatgg ctccggaggt ggtgctgggc aggagctgcg acgccaaggt cgacgtctgg    1740
agcagctgct gtatgatgct gcacatgctc aacggctgcc accctggac tcagttcttc    1800 cgagggccgc tctgcctcaa gattgccagc gagcctccgc ctgtgaggga gatcccaccc    1860
tcctgcgccc ctctcacagc ccaggccatc aagaggggc tgaggaaaga gcccatccac    1920
cgcgtgtctg cagcggagct gggagggaag gtgaaccggg cactacagca agtgggaggt    1980
ctgaagagcc cttggagggg agaatataaa gaaccaagac atccaccgcc aaatcaagcc    2040
aattaccacc agaccctcca tgcccagccg agagagcttt cgccaagggc cccagggccc    2100
cggccagctg aggagacaac aggcagagcc cctaagctcc agcctcctct cccaccagag    2160
cccccagagc caaacaagtc tcctcccttg actttgagca aggaggagtc tgggatgtgg    2220
gaacccttac ctctgtcctc cctggagcca gcccctgcca gaaacccag ctcaccagag    2280 cggaaagcaa ccgtcccgga gcaggaactg cagcagctgg aaatagaatt attcctcaac    2340
agcctgtccc agccattttc tctggaggag caggagcaaa ttctctcgtg cctcagcatc    2400
gacagcctct ccctgtcgga tgacagtgag aagaacccat caaaggcctc tcaaagctcg    2460
cgggacaccc tgagctcagg cgtacactcc tggagcagcc aggccgaggc tcgaagctcc    2520
agctggaaca tggtgctggc ccgggggcgg cccaccgaca ccccaagcta tttcaatggt    2580
gtgaaagtcc aaatacagtc tcttaatggt gaacacctgc acatccggga gttccaccgg    2640
gtcaaagtgg agacatcgc cactggcatc agcagccaga tcccagctgc agccttcagc    2700
ttggtcacca aagacgggca gcctgttcgc tacgacatgg aggtgccaga ctcgggcatc    2760
gacctgcagt gcacactggc ccctgatggc agcttcgcct ggagctggag ggtcaagcat    2820
ggccagctgg agaacaggcc ctaa                                           2844
```

<210> SEQ ID NO 3
<211> LENGTH: 33
<212> TYPE: PRT
<213> ORGANISM: NIK

<400> SEQUENCE: 3

```
Asp Phe Gly His Ala Val Cys Leu Gln Pro Asp Gly Leu Gly Lys Ser
1               5                   10                  15

Leu Leu Thr Gly Asp Tyr Ile Pro Gly Thr Glu Thr His Met Ala Pro
            20                  25                  30

Glu
```

<210> SEQ ID NO 4
<211> LENGTH: 32
<212> TYPE: PRT
<213> ORGANISM: MEKK1

<400> SEQUENCE: 4

Asp Phe Gly Ala Ala Ala Arg Leu Ala Ser Lys Gly Thr Gly Ala Gly
1               5                   10                  15

Glu Phe Gln Gly Gln Leu Leu Gly Thr Ile Ala Phe Met Ala Pro Glu
            20                  25                  30

<210> SEQ ID NO 5
<211> LENGTH: 31
<212> TYPE: PRT
<213> ORGANISM: MEKK2

<400> SEQUENCE: 5

Asp Phe Gly Ala Ser Lys Arg Leu Gln Thr Ile Cys Leu Ser Gly Thr
1               5                   10                  15

Gly Met Lys Ser Val Thr Gly Thr Pro Tyr Trp Met Ser Pro Glu
            20                  25                  30

<210> SEQ ID NO 6
<211> LENGTH: 31
<212> TYPE: PRT
<213> ORGANISM: MEKK3

<400> SEQUENCE: 6

Asp Phe Gly Ala Ser Lys Arg Leu Gln Thr Ile Cys Met Ser Gly Thr
1               5                   10                  15

Gly Ile Arg Ser Val Thr Gly Thr Pro Tyr Trp Met Ser Pro Glu
            20                  25                  30

<210> SEQ ID NO 7
<211> LENGTH: 26
<212> TYPE: PRT
<213> ORGANISM: MEK1

<400> SEQUENCE: 7

Asp Phe Gly Val Ser Gly Gln Leu Ile Asp Ser Met Ala Asn Ser Phe
1               5                   10                  15

Val Gly Thr Arg Ser Tyr Met Ser Pro Glu
            20                  25

<210> SEQ ID NO 8
<211> LENGTH: 26
<212> TYPE: PRT
<213> ORGANISM: MEK2

<400> SEQUENCE: 8

Asp Phe Gly Val Ser Gly Gln Leu Ile Asp Ser Met Ala Asn Ser Phe
1               5                   10                  15

Val Gly Thr Arg Ser Tyr Met Ala Pro Glu
            20                  25

<210> SEQ ID NO 9
<211> LENGTH: 27
<212> TYPE: PRT
<213> ORGANISM: MEK3

<400> SEQUENCE: 9

-continued

```
Asp Phe Gly Ile Ser Gly Tyr Leu Val Asp Ser Val Ala Lys Thr Met
1               5                   10                  15

Asp Ala Gly Cys Lys Pro Tyr Met Ala Pro Glu
                20              25

<210> SEQ ID NO 10
<211> LENGTH: 27
<212> TYPE: PRT
<213> ORGANISM: SEK1

<400> SEQUENCE: 10

Asp Phe Gly Ile Ser Gly Gln Leu Val Asp Ser Ile Ala Lys Thr Arg
1               5                   10                  15

Asp Ala Gly Cys Arg Pro Tyr Met Ala Pro Glu
                20              25
```